(12) United States Patent  
Fader et al.

(10) Patent No.: US 9,334,249 B2  
(45) Date of Patent: May 10, 2016

(54) INHIBITORS OF CYTOMEGALOVIRUS

(71) Applicant: Boehringer Ingelheim International GmbH, Ingelheim am Rhein (DE)

(72) Inventors: Lee Fader, New Milford, CT (US); Mathieu Parisien, Laval (CA); Carl Thibeault, Mascouche (CA); Louis Morency, Montréal (CA); Martin Duplessis, Somerville, MA (US); Clint James, Candiac (CA); Sébastien Morin, Montréal (CA); James Gillard, Rosemère (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/440,087

(22) PCT Filed: Oct. 31, 2013

(86) PCT No.: PCT/US2013/067674  
§ 371 (c)(1),  
(2) Date: May 1, 2015

(87) PCT Pub. No.: WO2014/070979  
PCT Pub. Date: May 8, 2014

(65) Prior Publication Data  
US 2015/0284348 A1 Oct. 8, 2015

Related U.S. Application Data

(60) Provisional application No. 61/722,152, filed on Nov. 3, 2012.

(51) Int. Cl.  
| C07D 417/12 | (2006.01) |
| C07D 277/56 | (2006.01) |
| C07D 413/12 | (2006.01) |
| C07D 417/14 | (2006.01) |
| C07D 277/82 | (2006.01) |

(52) U.S. Cl.  
CPC .......... *C07D 277/56* (2013.01); *C07D 277/82* (2013.01); *C07D 413/12* (2013.01); *C07D 417/12* (2013.01); *C07D 417/14* (2013.01)

(58) Field of Classification Search  
CPC .................................................... C07D 417/12  
USPC .......................................... 548/161; 514/367  
See application file for complete search history.

(56) References Cited

U.S. PATENT DOCUMENTS 6,166,028 A 12/2000 Bloom et al.

FOREIGN PATENT DOCUMENTS

| WO | 0034238 A1 | 6/2000 |
| WO | 0034261 A2 | 6/2000 |
| WO | 02085869 A1 | 10/2002 |
| WO | 2004014905 A1 | 2/2004 |
| WO | 2007059157 | 5/2007 |
| WO | 2008031534 A1 | 3/2008 |
| WO | 2009011850 A2 | 1/2009 |
| WO | 2010029300 A1 | 3/2010 |
| WO | 0034258 | 4/2010 |
| WO | 2010043377 A1 | 4/2010 |
| WO | 2010142752 A1 | 12/2010 |

OTHER PUBLICATIONS

Engers, Journal of Med. Chem, vol. 54, "Discovery, Synthesis, and Structure-Activity Relationship Development of a Series of N-(4-Acetamido)phenylpicolinamides as Positive Allosteric Modulatotors of Metabotropic Glutamate Receptor 4 (mGlu4) with CNS Exposure in Rats", 2011, p. 1106-1110.  
International Written Opinion, PCT ISA 237 for PCT US 2013067674.

*Primary Examiner* — Patricia L Morris  
(74) *Attorney, Agent, or Firm* — Michael P. Morris; Edward S. Lazer

(57) ABSTRACT

Compounds of Formula (I) wherein n, $R^1$, $R^{1.4}$, $R^2$, $R^4$ and Z are defined herein, are useful for the treatment of cytomegalovirus disease and/or infection.

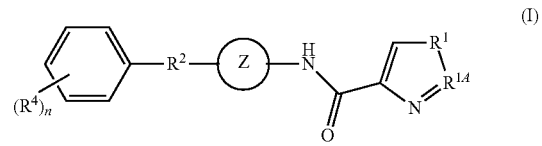

11 Claims, No Drawings

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggtgcag gtgccctg                                                    18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgtcgacga acgacgtacg                                                  20

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-ZEN
<220> FEATURE:
<223> OTHER INFORMATION: 3'-IABkFQ

<400> SEQUENCE: 3
tagacccgca tacaaa                                                      16

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acccactccc tcttagccaa tatt                                             24

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtagggctag gcccaccg                                                    18

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<223> OTHER INFORMATION: 5'-JOE
<220> FEATURE:
<223> OTHER INFORMATION: 3'-IABkFQ

<400> SEQUENCE: 6
ctagtctttg ccgcctgcga agca                                              24
```

INHIBITORS OF CYTOMEGALOVIRUS

SEQUENCE LISTING

The instant application contains a Sequence Listing which has been submitted electronically in ACII format and is hereby incorporated by reference in its entirety. Said ACII copy, created on Oct. 15, 2013, is named 13-0182_SL.txt and is 1,701 bytes in size.

FIELD OF THE INVENTION

The present invention relates to diamido arene analogs and their use as inhibitors of cytomegalovirus (CMV) replication, pharmaceutical compositions containing such analogs, and methods of using these analogs in the treatment and prevention of CMV disease and/or infection.

BACKGROUND OF THE INVENTION

CMV, a β-herpes virus, is a frequent and ubiquitous virus that affects all populations, worldwide, including adults and children with normal or compromised immune systems. CMV replication in the immunosuppressed host, if left unchecked, results in severe morbidity, mortality and other complications such as predisposition to bacterial and fungal infections, graft versus host disease and potential graft failure. CMV infection is the most common infection in patients undergoing hematopoietic stem cell transplantation (HCT) or solid organ transplantation (SOT). CMV is prevalent in 50-80% adult transplant candidates and found at lower prevalence in children. The current Gold Standard (Valganciclovir, Ganciclovir) is myelotoxic, and interferes with bone marrow engraftment in HCT. Therefore, its use in this population is limited to pre-emptive therapy, and the duration of its administration and the size of dose are often limited by its toxicity. This toxicity also limits the duration of prophylactic use and the dose in SOT. As a result, a new agent without the toxicities of Valganciclovir, Ganciclovir that allows for more effective prevention of CMV disease and transplant engraftment, and that substantially reduces treatment-related complications would represent a major break-through.

SUMMARY OF THE INVENTION

The present invention provides a novel series of compounds having inhibitory activity against CMV replication.

Further objects of this invention arise for the one skilled in the art from the following description and the examples.

An embodiment of the invention provides a compound of Formula (I) or racemate, enantiomer, diastereomer or tautomer thereof:

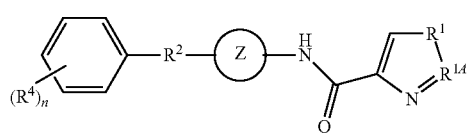

(I)

wherein
R$^1$ is S or O;
R$^{1A}$ is CH or N;
Ring Z is selected from the group consisting of phenyl, pyridine, pyridinone, benzimidazole and benzothiazole wherein each said phenyl, pyridine, pyridinone, benzimidazole and benzothiazole are optionally mono-, di- or tri-substituted with Z$^1$;

Z$^1$ is each independently selected from the group consisting of (C$_{1-6}$)alkyl, —(C$_{1-6}$)alkyl-(C$_{3-7}$)cycloalkyl, —(C$_{1-6}$)alkyl-heteroaryl, —(C$_{1-6}$)alkyl-heterocyclyl and —O—(C$_{1-6}$)alkyl;

R$^2$ is

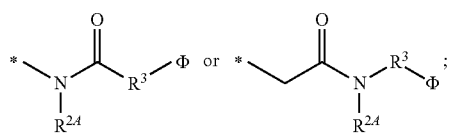

(wherein the site of attachment to the Z ring is indicated with * and the site of attachment to the phenyl ring is indicated with Φ);

R$^{2A}$ is H or (C$_{1-6}$)alkyl;

R$^3$ is absent, (C$_{3-7}$)cycloalkyl or (C$_{1-6}$)alkyl optionally mono-, di- or tri-substituted with R$^{3A}$;

R$^{3A}$ is each independently selected from the group consisting of halo, OH, —O—(C$_{1-6}$)alkyl, —C(=O)OH, —C(=O)NH$_2$, heterocycle, heteroaryl, —N(H)—(C$_{1-6}$)alkyl-heterocycle, —N(H)—(C$_{1-6}$)alkyl-heteroaryl, N(H)—C(=O)—O—(C$_{1-6}$)alkyl, —(C$_{3-7}$)cycloalkyl-C(=O)OH, —O-aryl and —O—(C$_{1-6}$)alkyl-aryl;

R$^4$ is halo, (C$_{1-6}$)haloalkyl, —CN, OH, —O—(C$_{1-6}$)alkyl or (C$_{1-6}$)alkyl, wherein each said alkyl is optionally mono- or di-substituted with OH, C(=O)OH, aryl, heterocycle or heteroaryl;

n is 0, 1, 2 or 3;

or a salt thereof.

Another embodiment of the invention provides a compound having the formula:

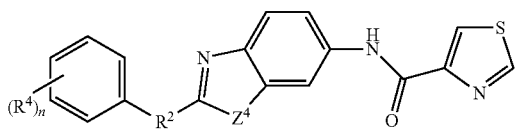

wherein R$^2$, R$^4$ and n are as defined above and Z$^4$ is S or N(H).

Another embodiment of the invention provides a compound having the formula:

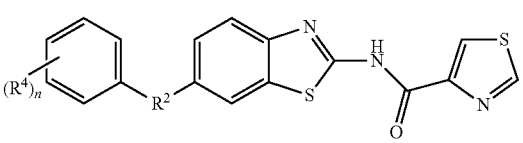

wherein R$^2$, R$^4$ and n are as defined above.

Another embodiment of the invention provides a compound having the formula:

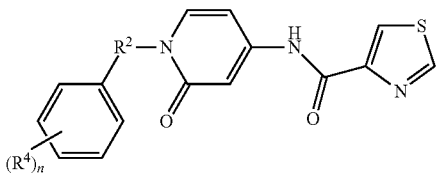

wherein $R^2$, $R^4$ and n are as defined above.

Another embodiment of the invention provides a compound having the formula:

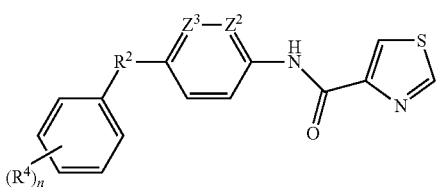

wherein $R^2$, $R^4$ and n are as defined above and one of $Z^2$ and $Z^3$ is N and the other of $Z^2$ and $Z^3$ is CH.

Another embodiment of the invention provides a compound having the formula:

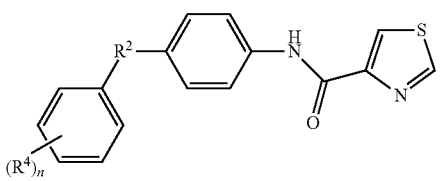

wherein $R^2$, $R^4$ and n are as defined above.

Another embodiment of this invention provides a compound of Formula (I), or a pharmaceutically acceptable salt thereof, as a medicament.

Also within the scope of this invention is the use of a compound of Formula (I), or a pharmaceutically acceptable salt thereof, for the manufacture of a medicament for the treatment or prevention of CMV disease and/or infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a CMV infection in a human being having or at risk of having the infection.

The invention also provides the use of a pharmaceutical composition as described hereinabove for the treatment of CMV disease in a human being having or at risk of having the disease.

Another aspect of the invention involves a method of treating or preventing CMV disease and/or infection in a human being by administering to the human being an anti-CMV virally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat CMV disease and/or infection; and packaging material comprising a label which indicates that the composition can be used to treat disease and/or infection by CMV; wherein the composition comprises a compound of formula (I) according to this invention or a pharmaceutically acceptable salt thereof.

Still another aspect of this invention relates to a method of inhibiting the replication of CMV comprising exposing the virus to an effective amount of the compound of formula (I), or a salt thereof, under conditions where replication of CMV is inhibited.

Further included in the scope of the invention is the use of a compound of formula (I), or a salt thereof, to inhibit the replication of CMV.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, with the $C_{1-3}$-alkyl group bound to the core. Unless specifically stated otherwise, for groups comprising two or more subgroups, the substituent may be attached to either subgroup.

In case a compound of the present invention is depicted in the form of a chemical name and as a formula in case of any discrepancy the formula shall prevail. An asterisk or the designation, ----, may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-3}$-alkyl embraces the radicals $H_3C$—, $H_3C$—$CH_2$—, $H_3C$—$CH_2$—$CH_2$— and $H_3C$—$CH(CH_3)$—.

The term "carbocyclyl" or "carbocycle" as used herein, either alone or in combination with another radical, means a mono-, bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms and all spiro, bridged and fused systems. Thus, the term "heterocyclyl" or "heterocyclyl" includes the following exemplary structures which are not depicted as radicals as each form may be attached through a covalent bond to any atom so long as appropriate valences are maintained:

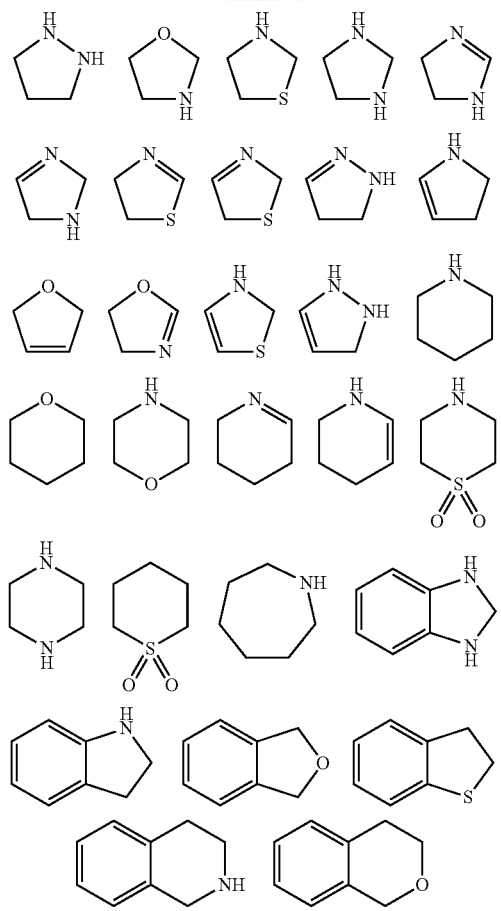

The term "heteroaryl" means a mono- or polycyclic-ring system containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms and all spiro, bridged and fused systems. Thus, the term "heteroaryl" includes the following exemplary structures which are not depicted as radicals as each form may be attached through a covalent bond to any atom so long as appropriate valences are maintained:

-continued

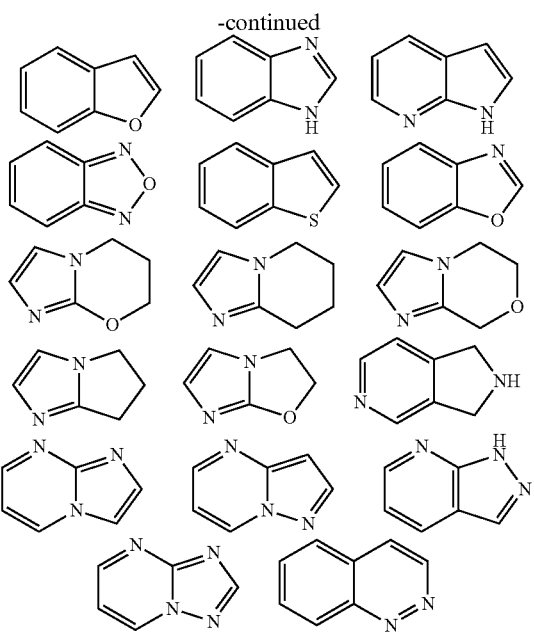

Many of the terms given above may be used repeatedly in the definition of a formula or group and in each case have one of the meanings given above, independently of one another.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

As used herein, the term "treatment" means the administration of a compound or composition according to the present invention to alleviate or eliminate symptoms of CMV disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Further Embodiments

In the following preferred embodiments, groups and substituents of the compounds of Formula (I) according to this invention are described in detail.

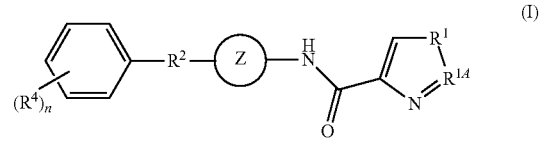

(I)

Any and each of the definitions below may be combined with each other.

$R^1$:
$R^1$-A: $R^1$ is O or S.
$R^1$—B: $R^1$ is O.
$R^1$—C: $R^1$ is S.
$R^{14}$:
$R^{14}$-A: $R^{14}$ is CH or N.
$R^{14}$—B: $R^{14}$ is N.
$R^{14}$—C: $R^{14}$ is CH.
Ring Z:
Ring Z-A: Ring Z is selected from the group consisting of phenyl, pyridine, pyridinone, benzimidazole and benzothiazole wherein each said phenyl, pyridine, pyridinone, benzimidazole and benzothiazole are optionally mono-, di- or tri-substituted with $Z^1$;

$Z^1$ is each independently selected from the group consisting of $(C_{1-6})$alkyl, —$(C_{1-6})$alkyl-$(C_{3-7})$cycloalkyl, —$(C_{1-6})$alkyl-heteroaryl, —$(C_{1-6})$alkyl-heterocyclyl and —O—$(C_{1-6})$alkyl.

Ring Z-B: Ring Z is selected from the group consisting of phenyl, pyridine, pyridinone, benzimidazole and benzothiazole.

Ring Z-C: Ring Z is selected from the group consisting of phenyl, pyridine and pyridinone.

Ring Z-D: Ring Z is selected from the group consisting of benzimidazole and benzothiazole.

$R^2$:

$R^2$-A: $R^2$ is

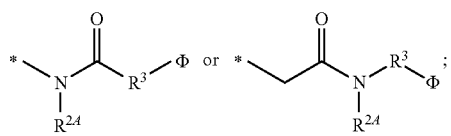

(wherein the site of attachment to the Z ring is indicated with * and the site of attachment to the phenyl ring is indicated with Φ);

$R^{2A}$ is H or $(C_{1-6})$alkyl;

$R^3$ is absent, $(C_{3-7})$cycloalkyl or $(C_{1-6})$alkyl optionally mono-, di- or tri-substituted with $R^{3A}$;

$R^{3A}$ is each independently selected from the group consisting of halo, OH, —O—$(C_{1-6})$alkyl, —C(=O)OH, —C(=O)NH$_2$, heterocycle, heteroaryl, —N(H)—$(C_{1-6})$alkyl-heterocycle, —N(H)—$(C_{1-6})$alkyl-heteroaryl, N(H)—C(=O)—O—$(C_{1-6})$alkyl, —$(C_{3-7})$cycloalkyl-C(=O)OH, —O-aryl and —O—$(C_{1-6})$alkyl-aryl.

$R^2$—B: $R^2$ is

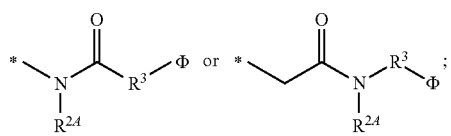

(wherein the site of attachment to the Z ring is indicated with * and the site of attachment to the phenyl ring is indicated with Φ);

$R^{2A}$ is H or $(C_{1-6})$alkyl;

$R^3$ is absent or $(C_{1-6})$alkyl optionally mono-, di- or tri-substituted with $R^{3A}$;

$R^{3A}$ is each independently selected from the group consisting of OH, —O—$(C_{1-6})$alkyl, —O-aryl and —O—$(C_{1-6})$alkyl-aryl.

$R^2$—C: $R^2$ is

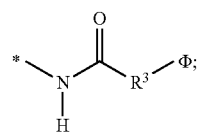

(wherein the site of attachment to the Z ring is indicated with * and the site of attachment to the phenyl ring is indicated with Φ);

$R^3$ is absent or $(C_{1-6})$alkyl optionally mono-, di- or tri-substituted with $R^{3A}$;

$R^{3A}$ is each independently selected from the group consisting of OH, —O—$(C_{1-6})$alkyl, —O-aryl and —O—$(C_{1-6})$alkyl-aryl.

$R^4$:

$R^4$-A: $R^4$ is halo, $(C_{1-6})$haloalkyl, —CN, OH, —O—$(C_{1-6})$alkyl or $(C_{1-6})$alkyl, wherein each said alkyl is optionally mono- or di-substituted with OH, C(=O)OH, aryl, heterocycle or heteroaryl.

$R^4$—B: $R^4$ is halo, $(C_{1-6})$haloalkyl, —CN or $(C_{1-6})$alkyl.

$R^4$—C: $R^4$ is halo or $(C_{1-6})$haloalkyl.

n:

n-A: n is 0, 1, 2 or 3.

n-B: n is 0, 1 or 2.

n-C: n is 1 or 2.

Further subgeneric embodiments of the present invention are set forth in the following table, wherein each substituent group of each embodiment is defined according to the definitions set forth above:

| Embodiment | $R^1$ | $R^{1A}$ | $R^2$ | $R^4$ | Z | n |
|---|---|---|---|---|---|---|
| E-1 | $R^1$-C | $R^{1A}$-C | $R^{2C}$- | $R^4$-C | Z-C | n-C |
| E-2 | $R^1$-C | $R^{1A}$-C | $R^{2C}$- | $R^4$-C | Z-D | n-C |
| E-3 | $R^1$-A | $R^{1A}$-A | $R^2$-B | $R^4$-B | Z-C | n-B |
| E-4 | $R^1$-A | $R^{1A}$-A | $R^2$-B | $R^4$-B | Z-D | n-B |
| E-5 | $R^1$-A | $R^{1A}$-A | $R^2$-C | $R^4$-B | Z-B | n-A |

Examples of most preferred compounds according to this invention are each single compound in Tables 1.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

Suitable injectables may be obtained, for example, by mixing one or more compounds according to the invention with known excipients, for example inert diluents, carriers, co-solvent, adjuvants, surfactants and/or cyclodextrin complex. The injectable formulation may be an emulsion or suspension.

Combination Therapy

Combination therapy is contemplated wherein a compound of the invention, or a pharmaceutically acceptable salt thereof, is co-administered with at least one additional agent selected from: a CMV entry inhibitor, a CMV early transcription event inhibitor, a CMV helicase-primase inhibitor, a CMV DNA polymerase inhibitor, an inhibitor of UL97 kinase, a CMV protease inhibitor, a CMV terminase inhibitor, a CMV maturation inhibitor, an inhibitor of another target in the CMV life cycle, a CMV vaccine and a CMV biological agent.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

Antiviral agents contemplated for use in such combination therapy include agents (compounds or biologicals) that are effective to inhibit the production and/or replication of a virus in a human being, including but not limited to agents that interfere with either host or viral mechanisms necessary for the production and/or replication of a virus in a human being. Such agents can be selected from: a CMV entry inhibitor; a CMV early transcription event inhibitor; a CMV helicase-primase inhibitor; a CMV DNA polymerase inhibitor such as Ganciclovir (Cytovene), Valganciclovir (Valcyte; Cymeval), Cidofovir (Vistide), Foscarnet (Foscavir), CMX001, cyclopropavir (MBX-400) and Valaciclovir (Valtrex; Zelitrex); an inhibitor of UL97 kinase such as Maribavir; a CMV protease inhibitor; a CMV terminase inhibitor such as AIC246 (Letermovir); a CMV maturation inhibitor; other inhibitors such as Artesunate; a CMV vaccine such as TransVax and a CMV biological agent such as Cytogam (Cytotect), TCN-202 and CMV IgG.

EXAMPLES

Other features of the present invention will become apparent from the following non-limiting examples which illustrate the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. The reactants used in the examples below may be obtained either as described herein, or if not described herein, are themselves either commercially available or may be prepared from commercially available materials by methods known in the art. Mass spectral analyses may be recorded using an electrospray mass spectrometer.

Compounds and intermediates can be purified by a Teledyne ISCO Combiflash $R_f$ System at 254 nm using commercial normal phase silica 4-120 g Redisep $R_f$ or Silicycle columns at a flow rate of 18-85 mL/min depending on column size. Mass spectral analyses may be recorded using flow injection analysis mass spectrometry or Waters Acquity Ultraperformance LC System consisting of a sample organizer, PDA detector, column manager, sample manager, binary solvent manager and SQ detector.

Reactions performed in microwave conditions are conducted in a Biotage Initiator 2.0 microwave synthesizer equipped with a Robot Sixty for vial manipulations. The temperature range is from 40-250° C. The pressure range is from 0-20 bar and the power range is from 0-400 Watts at 2.45 GHz. The vial size varies from 0.5 mL to 20 mL. The solvent absorption level is high by default. Specific reaction times and temperatures are given in the experimental section when applicable.

Preparative RP-HPLC is performed under standard conditions using one of the following specific measuring conditions:

A) Waters SunFire Prep OBD C18 column (5 μm, 19×50 mm) eluting firstly with a hold period of 1 min in initial gradient condition then eluting with a linear MeOH gradient containing 10 mM Ammonium Formate (pH 3.8) over 10 min at 30 mL/min. Fractions containing the desired product are pooled, concentrated and lyophilized.

B) Waters XBridge Prep OBD C18 column (5 μm, 19×50 mm) eluting firstly with a hold period of 1 min in initial gradient condition then eluting with a linear MeOH gradient containing 10 mM Ammonium Bicarbonate (pH 10.0) over 10 min at 30 mL/min. Fractions containing the desired product are pooled, concentrated and lyophilized.

C) Waters SunFire Prep OBD C18 column (5 μm, 19×50 mm) eluting firstly with a hold period of 1 min in initial gradient condition then eluting with a linear MeCN gradient containing 0.06% TFA (v/v) over 10 min at 30 mL/min. Fractions containing the desired product are pooled and lyophilized.

D) Waters XBridge Prep OBD C18 column (5 μm, 19×50 mm) eluting firstly with a hold period of 1 min in initial gradient condition then eluting with a linear MeCN gradient containing 10 mM Ammonium Bicarbonate (pH 10.0) over 10 min at 30 mL/min. Fractions containing the desired product are pooled and lyophilized.

E) Waters SunFire Prep OBD C18 column (5 μm, 19×50 mm) eluting firstly with a hold period of 0.5 min in initial gradient condition then eluting with a linear MeCN gradient containing 10 mM Ammonium Formate (pH 3.8) over 6.9 min at 45 mL/min. The eluents are warmed at 45° C. using a Timberline Instrument TL600 Mobile Phase Heater during the whole run. Fractions containing the desired product are pooled and lyophilized.

F) Waters XSelect Prep CSH OBD C18 column (5 μm, 30×75 mm) eluting firstly with a hold period of 0.5 min in initial gradient condition then eluting with a linear MeCN gradient containing 0.1% formic acid (v/v) over 6.4 min at 60 mL/min. The eluents are warmed at 45° C. using a Timberline Instrument TL600 Mobile Phase Heater during the whole run. Fractions containing the desired product are pooled and lyophilized.

Analytical UPLC is performed under standard conditions using one of the following specific measuring conditions:

A) Waters ACQUITY UPLC BEH C18 column (1.7 μm, 2.1×30 mm) eluting with a linear MeOH gradient containing 10 mM Ammonium Bicarbonate (pH 10) over 2.2 min at 0.75 mL/min.

B) Waters ACQUITY UPLC HSS C18 column (1.8 μm, 2.1×30 mm) eluting with a linear MeOH gradient containing 10 mM Ammonium Formate (pH 3.8) over 2.3 min at 0.8 mL/min.

C) Waters ACQUITY UPLC HSS C18 column (1.8 μm, 2.1×30 mm) eluting with a linear MeCN gradient containing 0.06% TFA (v/v) over 2.2 min at 0.9 mL/min.

D) Waters ACQUITY UPLC BEH C18 column (1.7 μm, 2.1×30 mm) eluting with a linear MeCN gradient containing 10 mM Ammonium Bicarbonate (pH 10) over 2.2 min at 0.75 mL/min.

E) Waters ACQUITY UPLC HSS C18 column (1.8 μm, 2.1× 30 mm) eluting with a linear MeCN gradient containing 10 mM Ammonium Formate (pH 3.8) over 2.3 min at 0.8 mL/min. The eluents are warmed at 45° C. using a column preheater during the whole run.

F) Waters XSelect UPLC CSH C18 column (1.7 μm, 2.1×30 mm) eluting with a linear MeCN gradient containing 0.1% formic acid (v/v) over 2.0 min at 0.9 mL/min. The eluents are warmed at 45° C. using a column preheater during the whole run.

Abbreviations used in the examples include:
Ac: acetyl; AcOH: acetic acid; BEH: ethylene bridged hybrid; BOC or Boc: tert-butyloxycarbonyl; Bu: butyl; dba: dibenzylideneacetone; DCE: 1,2-dichloroethane; DCM: dichloromethane; DIPEA: diisopropylethylamine; DMEM: Dulbecco's modified Eagle's medium; DMF: N,N-dimethylformamide; DMSO: dimethylsulfoxide; dppf: 1,1'-diphenylphosphinylferrocene; eq or equiv: equivalents; Et: ethyl; Et$_2$O: diethyl ether; EtOAc: ethyl acetate; EtOH: ethanol; HATU: [0-(7-azabenzotriazol-1-yl)-1,1,3,3-tetramethyluronium hexafluorophosphate]; Hex: hexanes; HPLC: high performance liquid chromatography; HSS: high strength silica; $^i$Pr or i-Pr: 1-methylethyl (iso-propyl); iPrOH: isopropanol; Me: methyl; MeCN: acetonitrile; MeOH: methanol; MS: mass spectrometry; [M+H]$^+$: protonated molecular ion; MTBE or t-MBE: tert-butylmethyl ether; OBD: optimum bed density; PDA: photodiode array; Ph: phenyl; Pr: propyl; RP: reverse phase; RT: room temperature (18 to 22° C.); tert-butyl or t-butyl: 1,1-dimethylethyl; TEA: triethylamine; TFA: trifluoroacetic acid; THF: tetrahydrofuran; t$_R$: retention time and UPLC: ultraperformance liquid chromatography; Xantphos: 4,5-bis(diphenylphosphino)-9,9-dimethylxanthene Example A1

Preparation of Compound A1b

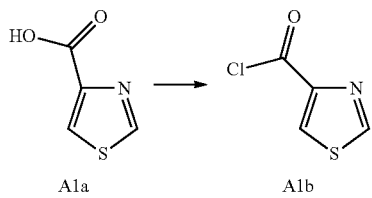 [SMILES: O=C(O)c1cscn1 ; O=C(Cl)c1cscn1]

A suspension of A1a (10.0 g, 77.4 mmol, Combi Blocks) in DCM (100 mL) is treated with oxalyl chloride (66.0 mL, 619.5 mmol). Then, DMF (599.6 μL, 7.7 mmol) is added dropwise. The reaction mixture is stirred overnight at RT, and then concentrated under reduced pressure, azeotroped with toluene (150 mL) and dried under high vacuum for 1 h to afford A1b which is used as is in subsequent reactions.

Example A2

Preparation of Compound A2c

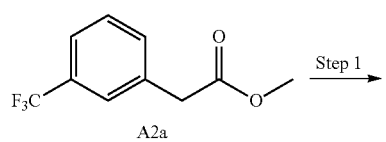

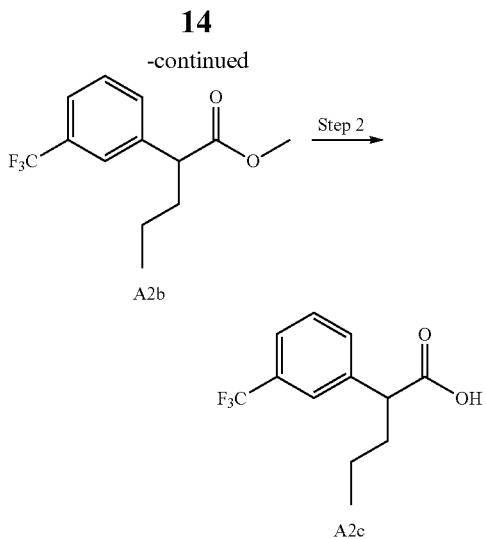

Step 1:
A solution of A2a (1.0 g, 4.6 mmol) in THF (10 mL) is added to a stirred solution of KHMDS (1.1 g, 5.7 mmol) in THF (20 mL) that is cooled to −78° C. The reaction is stirred for 30 min and then propyliodide (136.4 μL, 2.2 mmol) is added. The reaction is stirred for 45 min, warmed to RT and stirred for 2.5 h. The reaction is diluted with saturated NH$_4$Cl, extracted with EtOAc (3×), dried over Na$_2$SO$_4$ and the solvent is removed on the rotovap. The crude mixture is purified by Combiflash to afford A2b.

Step 2:
To a solution of A2b (600 mg, 2.5 mmol) in THF (2 mL) is added NaOH (10 M, 1.1 mL, 10 mmol) and the reaction is stirred for 3 h. The mixture is concentrated and then is extracted with Et$_2$O. The aqueous phase is acidified to pH 2 with concentrated HCl and extracted with EtOAc. The organic layer is washed with brine, dried over Na$_2$SO$_4$, filtered, and concentrated to provide A2c.

Example A3

Preparation of Compound A3b

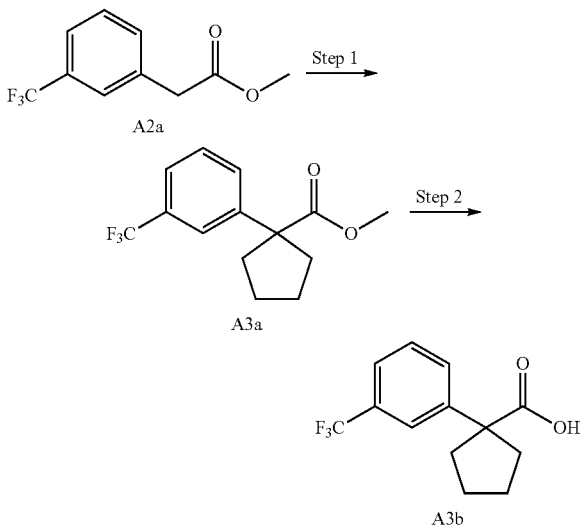

Step 1:

A solution of A2a (2.0 g, 9.2 mmol) in DMSO (12 mL) is cooled to 0° C. and treated with solid NaH (60% dispersion in mineral oil, 1.1 g, 44 mmol). The reaction is stirred for 15 min and then 1,4-dibromobutane (1.3 mL, 12 mmol) is added. The reaction is warmed to RT and stirred overnight. The reaction is diluted with water, extracted with EtOAc (2×), dried over $Na_2SO_4$ and the solvent is removed on the rotovap. The crude mixture is purified by Combiflash to give A3a.

Step 2:

Compound A3b is prepared from A3a by analogy to the preparation of compound A2c, following step 2 from Example A2.

Example A4

Preparation of Compound A4b

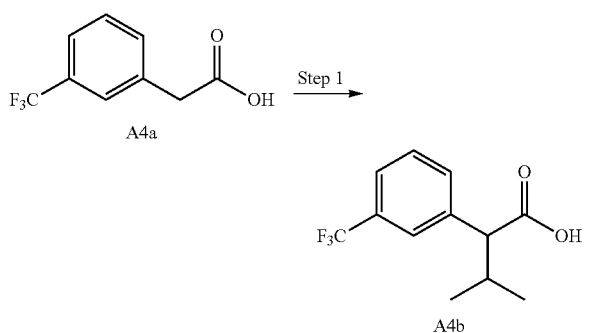

Step 1:

Compound A4a (Aldrich, 180 mg, 0.86 mmol) in THF (5 mL) is cooled to 0° C. and treated with n-BuLi (2.5M in hexanes, 1.4 mL, 3.4 mmol) and the reaction is stirred for 15 min. Isopropyliodide (0.34 mL, 3.4 mmol) is added over 10 min and the reaction is allowed to come to RT and is stirred overnight. The reaction is diluted with saturated $NH_4Cl$ and extracted with EtOAc. The organic layer is dried over $MgSO_4$ and concentrated to give A4b.

Example B1

Preparation of Compound 1001

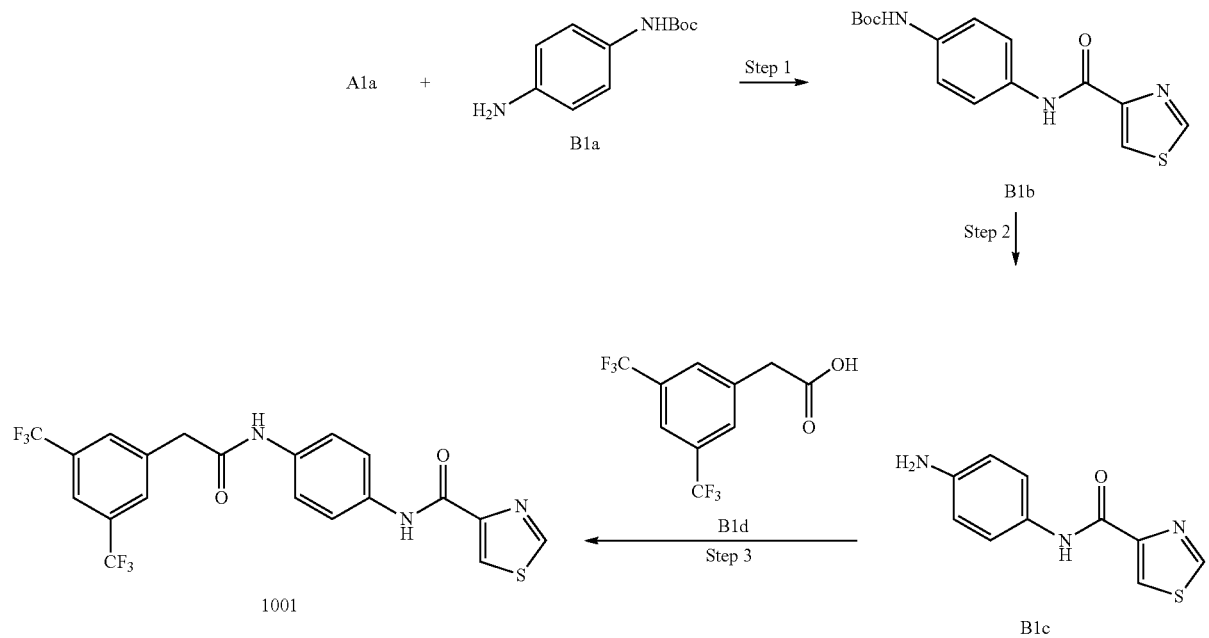

Step 1:

A solution of DIPEA (13 mL, 72 mmol), A1a (4.8 g, 37 mmol) and B1a (6.0 g, 29 mmol, Senn Chemicals AG) in DMF (60 mL) is treated with HATU (15 g, 40 mmol) at RT. The reaction is stirred for 1 h and then is diluted with water and EtOAc. The organic layer is separated, washed with water (2×), dried over $MgSO_4$ and evaporated to dryness. The product is purified by Combiflash to give B1 b.

Step 2:

Carbamate B1 b (5.4 g, 17 mmol) is dissolved in DCM (54 mL) at RT and treated with TFA (54 mL). This mixture is stirred overnight and then concentrated to dryness. The residue is taken up in EtOAc and washed with 1N NaOH and brine, dried over $MgSO_4$ and concentrated to dryness to give B1c.

Step 3:

A solution of DIPEA (0.15 mL, 0.86 mmol), B1d (Oakwood, 100 mg, 0.38 mmol) and B1c (75 g, 0.34 mmol) in DMF (10 mL) is treated with HATU (180 mg, 0.48 mmol). The reaction is stirred for 3 d and then is diluted with an aqueous saturated solution of $NH_4Cl$ and EtOAc. The organic layer is separated, washed with water (2×), dried over $MgSO_4$ and evaporated to dryness. The product is triturated with DCM and then recrystalized from MeOH to give compound 1001.

Example B2

Preparation of Compound 1122

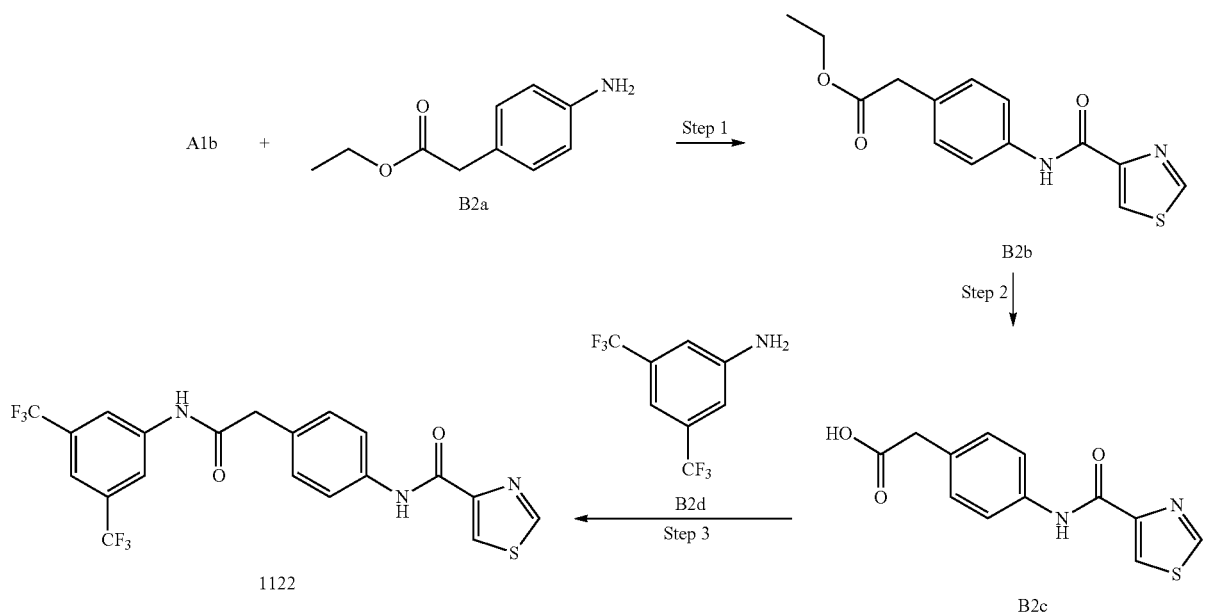

Step 1:
A suspension of A1b (870 mg, 5.7 mmol) and B2a (Maybridge, 780 mg, 4.4 mmol) in DCM (40 mL) is treated with TEA (1.2 mL, 8.7 mmol). After 20 min, the reaction is concentrated to afford B2b, which is used as is in the next step.

Step 2:
A solution of B2b (1.3 g, 4.3 mmol) in THF (15 mL) and MeOH (7.5 mL) is treated with aqueous NaOH (5N, 3.9 mL, 19 mmol) and the reaction is stirred at RT for 20 min. The reaction is concentrated. The residue is taken up in EtOAc and washed with diluted a 10% citric acid solution (2×). The organic layer is dried over MgSO$_4$ and concentrated to give B2c.

Step 3:
A solution of DIPEA (0.13 mL, 26 mmol), B2c (50 mg, 0.19 mmol) and B2d (44 mg, 0.19 mmol, Aldrich) in DMF (2 mL) at RT is treated with HATU (89 mg, 0.19 mmol) and the reaction is stirred for 1 h. The reaction is diluted with DMSO and the product purified by preparative HPLC to give compound 1122.

Example B3

Preparation of Compound 1027

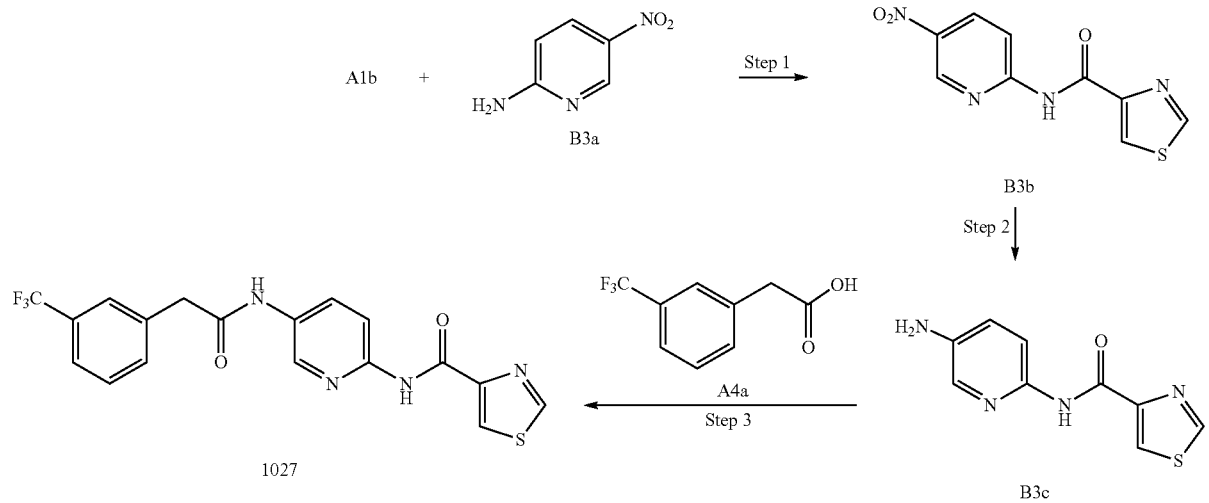

Step 1:
Compound B3b is prepared from B3a (Combiblocks) by analogy to compound B2b, following step 1 from Example B2.

Step 2:
Compound B3b (450 mg, 1.8 mmol) is dissolved in EtOH (100 mL) and the flask is evacuated and backfilled with N$_2$. Pd—C(Aldrich, 5% w/w, 380 mg, 0.18 mmol) is added and the flask is evacuated and backfilled with H$_2$ (1 atm). The reaction is stirred for 3 d and then the flask is flushed with N$_2$. The mixture is diluted with EtOAc and then filtered through a pad of Celite (with EtOAc washings). The filtrate is evaporated to dryness to give B3c.

Step 3:
Compound 1027 is prepared from A4a and B3c by analogy to compound 1001, following step 3 from Example B1.

Example B4

Preparation of Compound 1131

Step 2:
Compound B4b (250 mg, 1.3 mmol), tert-butylcarbamate (Aldrich, 473 mg, 4.0 mmol), Cs$_2$CO$_3$ (Aldrich, 658 mg, 2.0 mmol), Pd$_2$(dba)$_3$ (Strem, 123 mg, 0.14 mmol) and Xantphos (Strem, 156 mg, 0.27 mmol) are suspended in THF (5 mL) and the mixture degassed by bubbling N$_2$ through with sonication for 5 min. The reaction is t sealed (Schlenck tube) and heated to 70° C. overnight. The mixture is cooled to RT, filtered and the filtrate is concentrated. The residue is partitioned between EtOAc and a saturated aqueous solution of NaHCO$_3$. The organic layer is washed with water and brine, dried over MgSO$_4$, and concentrated. The product is purified by Combiflash to give B4c.

Step 3:
Carbamate B4c (5.4 g, 17 mmol) is dissolved in DCM (54 mL) and diluted slowly with TFA (54 mL). This mixture is stirred overnight and then concentrated to dryness. The residue is taken up in EtOAc and washed with 1N NaOH and brine and then is dried over MgSO$_4$ and concentrated to dryness to give B4d.

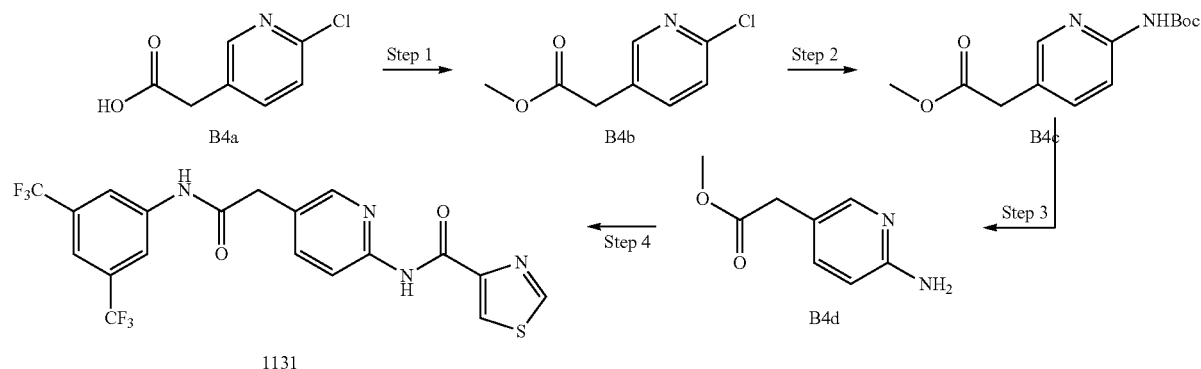

Step 1:
Compound B4a (5.0 g, 29 mmol) is dissolved in MeOH (50 mL) and sulfuric acid (1.9 mL) is added. The reaction is stirred at RT for 45 min and then is concentrated. The residue is partitioned between EtOAc and saturated NaHCO$_3$. The organic layer is washed with water and brine, dried over MgSO$_4$, filtered and concentrated to give B4b.

Step 4:
Compound 1131 is prepared from B4d by analogy to the preparation of compound 1122 from compound B2d following steps 2 and 3 from Example B2.

Example B5

Preparation of Compound 1148

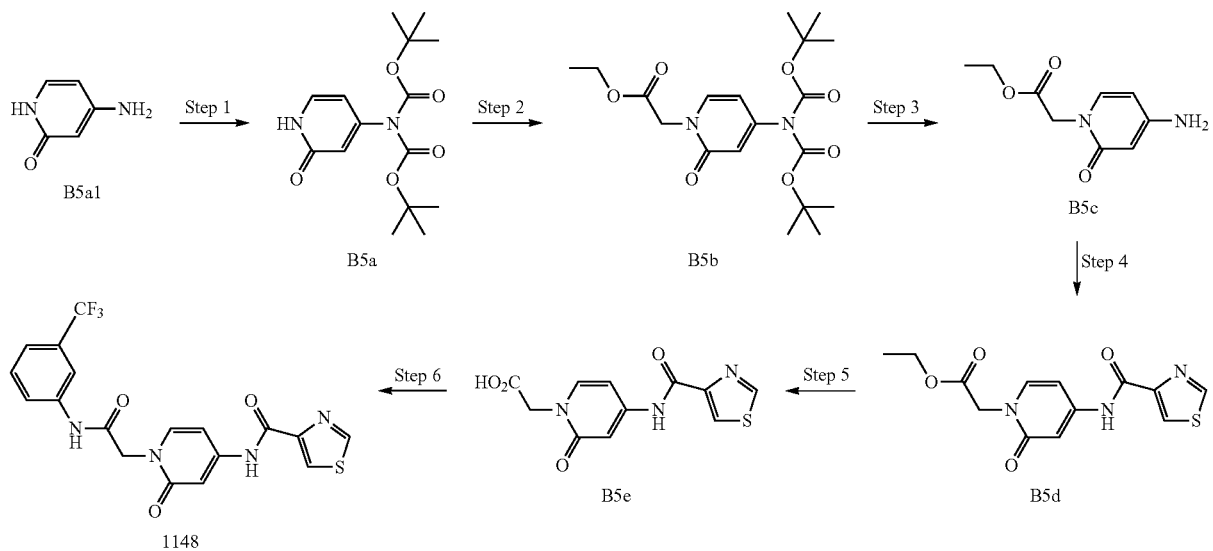

Step 1:

Solid Boc$_2$O (28 g, 130 mmol) is added to a solution of B5a1 (Aconpharm, 4.0 g, 36 mmol, Tyger) in MeCN (250 mL). Solid DMAP (250 mg, 2.0 mmol) is added in 50 mg portions at 20 min intervals. The reaction is stirred overnight and then concentrated, diluted with 1:1 t-BME/EtOAc and washed with 10% citric acid, saturated NaHCO$_3$ and brine. The organic layer is dried over Na$_2$SO$_4$ and evaporated to dryness. MeOH (80 mL) and saturated NaHCO$_3$ (40 mL) are added and the mixture is stirred 3 d. The reaction is filtered and the filter cake is washed with MeOH. The filtrate is evaporated and the residue is taken up in EtOAc and the solution is washed with water and brine. The organic layer is dried over Na$_2$SO$_4$ and concentrated and the product purified by Combiflash to give B5a.

Step 2:

Solid NaH (60% dispersion in mineral oil, 280 mg, 1.1 mmol) is added to a suspension of B5a (2.0 g, 6.4 mmol) in THF (30 mL) at 0° C. Ethyl bromoacetate (0.86 mL, 7.7 mmol) is added to the reaction, which is stirred for 1 h, allowed to warm to RT, and then stirred for an additional 4 h. The mixture is diluted with EtOAc and is washed with water, saturated NaHCO$_3$ and brine. The organic layer is dried over Na$_2$SO$_4$, concentrated and the product purified by Combiflash to give B5b.

Step 3:

Compound B5b (2.3 g, 5.9 mmol) in DCM (4 mL) is treated with TFA (4 mL) and the reaction is stirred for 20 h. The reaction is evaporated and the residue taken up in TFA (4 mL) and is stirred for 2 h at RT. The reaction is concentrated to dryness and t-BME (20 mL) and hexanes (20 mL) are added. The resulting mixture is stirred for 2 h and the solid is collected by filtration to give B5c.

Step 4:

A solution of B5c (750 mg, 2.4 mmol) in THF (10 mL) is treated sequentially with A1b (430 mg, 2.9 mmol) and DIPEA (0.84 mL, 4.8 mmol). The reaction is stirred overnight at RT and then 4 h at 65° C. The reaction is cooled to RT, evaporated to dryness and then water (3 mL) and NaOH (5M, 3 mL, 15 mmol) are added. The reaction is stirred for 2 h and then made acidic with HOAc. This solution is used directly to purify the product by preparative HPLC to give B5d.

Step 5:

Compound B5d (409 mg, 1.3 mmol) is dissolved into MeOH (5 mL) at RT and is treated with 1M NaOH (2 mL, 2 mmol). The resulting mixture is stirred at RT for 2 h, acidified using 1N HCl and cooled to 0° C. The residue is filtered and washed with cold water to afford B5e.

Step 6:

Carboxylic acid B5e (20 mg, 0.072 mmol) in MeCN (2 mL) is treated sequentially with 3-trifluoromethylaniline (Acros, 23 mg, 0.14 mmol), DBU (21 µL, 0.14 mmol) and 4-(4,6-dimethoxy-1,3,5-triazin-2-yl)-4-methylmorpholinium chloride (40 mg, 0.14 mmol). The reaction is stirred overnight and then used directly to purify the product by preparative HPLC to give compound 1148.

Example B6

Preparation of Compound 1143

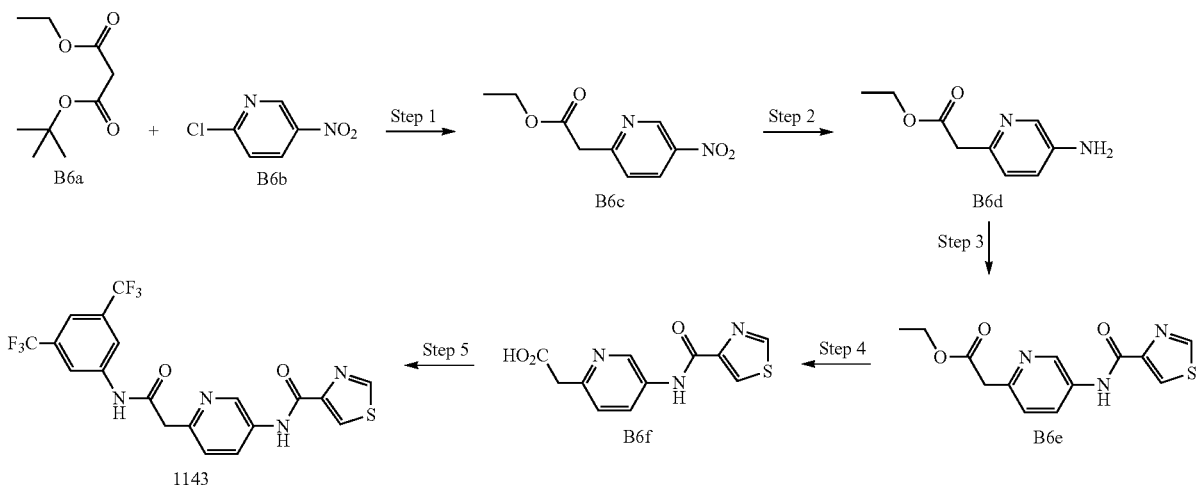

Step 1:

Solid NaH (60% dispersion in mineral oil, 1.8 g, 45 mmol) is added to a mixture of malonate diester B6a (Oakwood, 7.8 mL, 42 mmol) in THF (100 mL) at 0° C. The reaction is stirred for 20 min and then chloropyridine B6b (Aldrich, 5.1 g, 32 mmol) is added and the reaction is stirred overnight. The reaction is concentrated and the residue dissolved in t-BME. This solution is washed with 10% citric acid, 10% NaHCO$_3$ and brine. The organic layer is dried over Na$_2$SO$_4$, concentrated and the product purified by Combiflash. The aryl malonate intermediate is then taken up in 2:1 DCM/TFA (30 mL/15 mL) and this solution is stirred for 2 h. The solution is evaporated to dryness. The residue taken up in t-BME and washed (2×) with 10% NaHCO$_3$ and brine. The organic layer is dried over Na$_2$SO$_4$ and evaporated and the product purified by Combiflash to give B6c.

Step 2:

A flask containing a solution of B6c (4.0 g, 19 mmol) in EtOH (50 mL) is evacuated and backfilled with N$_2$. Pd/C (10% w/w, 400 mg) is added and the flask evacuated and backfilled with H$_2$ gas (1 atm). The reaction is stirred for 3 d and then the flask is evacuated and backfilled with N$_2$. The mixture is filtered through celite and then the filtrate is evaporated to dryness. t-BME is added and 4M HCl/dioxane (4M, 5 mL, 20 mmol) is added with stirring. EtOH (10 mL) is added and the mixture sonicated. The solid is collected by filtration to give B6d.

Step 3:

A solution of A1b (300 mg, 2.0 mmol) in DCM (10 mL) is treated with amine B6d (500 mg, 2.3 mmol) followed by DIPEA (1.0 mL, 5.7 mmol) and the reaction is stirred overnight. The reaction is diluted with t-BME and EtOAc and washed with 10% citric acid, saturated $NaHCO_3$ and brine. The mixture is filtered and the filtrate evaporated to dryness. The product is purified by Combiflash to give B6e.

Step 4:

A solution of B6e (480 mg, 1.6 mmol) in DMSO (4 mL) is treated with NaOH (5M, 1.6 mL, 8 mmol). The reaction is stirred for 2 h and then is diluted with water (30 mL). This mixture is made acidic (pH=2) with 4N HCl and the resulting suspension is stirred for 30 min. The solid is collected by filtration, washed with water and dried to give B6f.

Step 5:

Compound 1143 is prepared from compounds B6f and B2d by analogy to the preparation of compound 1122 from compound B2c in Example B2.

Example B7

Preparation of Compound 1158

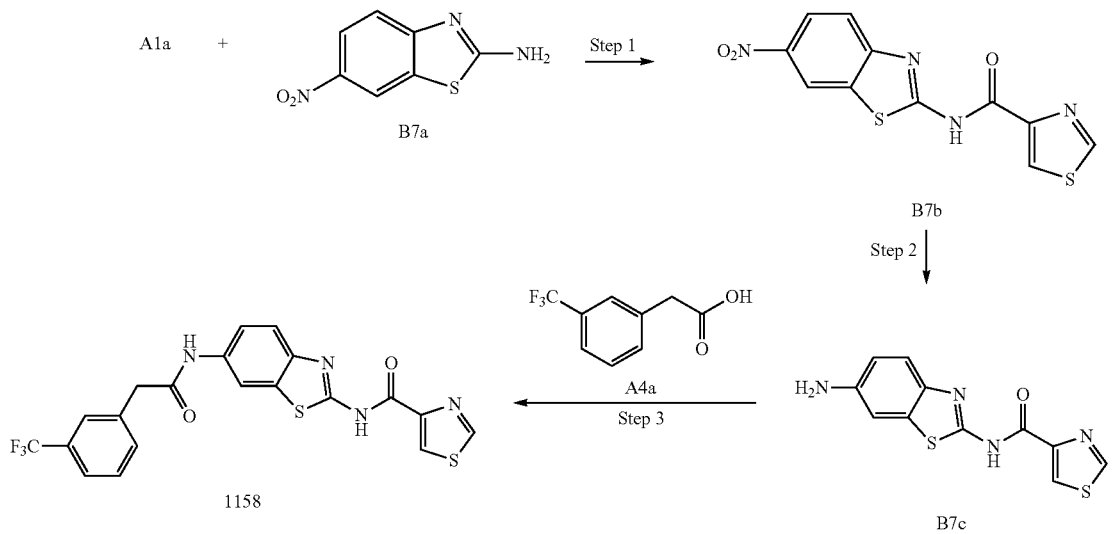

Step 1:

Compound A1a (5.0 g, 26 mmol) and B7a (Lancaster, 4.3 g, 33 mmol) and DIPEA (14 mL, 79 mmol) are dissolved in DMF (100 mL) and HATU (14 g, 36 mmol) is added. The reaction is stirred overnight and then is poured into water. The resulting precipitate is collected by filtration to give B7b.

Step 2:

Compound B7b (5.2 g, 17 mmol) is dissolved in MeOH (200 mL) and the flask is evacuated and backfilled with $N_2$. Pd—C (Aldrich, 5% w/w, 5 g, 2.3 mmol) is added and the flask is evacuated and backfilled with $H_2$ (1 atm). The reaction is stirred overnight and then the flask is flushed with $N_2$. The mixture is filtered through a pad of Celite. The filtrate is evaporated to dryness to give B7c.

Step 3:

Compound 1158 is prepared from A4a and B7c by analogy to compound 1001, following step 3 from Example B1.

Example B8

Preparation of Compound 1098

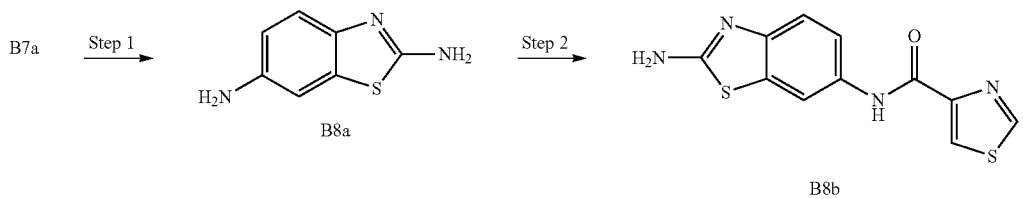

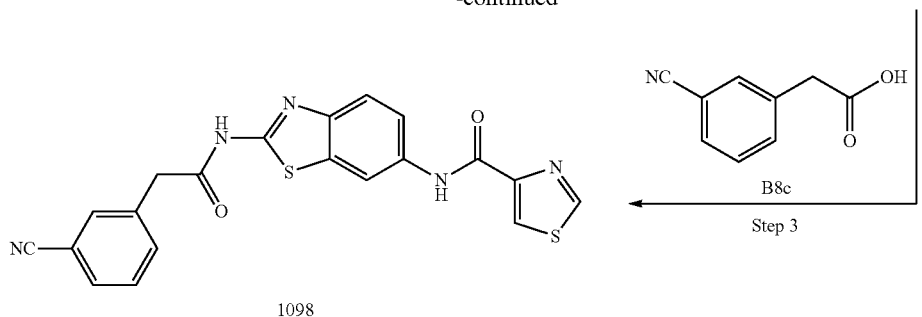

Step 1:

To solution of B7a (10 g, 51 mmol, Lancaster) dissolved in THF (300 mL) and HCl (2N, 150 mL) is added Sn powder (20 g, 170 mmol). The reaction mixture is heated to 50° C. and stirred for 1 h. The reaction is cooled to RT and then is diluted with NaOH (10N, 20 mL) and saturated NaHCO$_3$ (20 mL). This mixture is filtered through Celite and the filtrate is diluted with EtOAc. The organic layer is washed with brine, dried over Na$_2$SO$_4$ and concentrated to give B8a.

Step 2:

Compound A1a (580 mg, 4.5 mmol, Combi Blocks) and B8a (750 mg, 4.5 mmol) and DIPEA (1.7 mL, 9.5 mmol) are dissolved in DMF (30 mL). TBTU (1.6 g, 5.0 mmol) is added and the reaction is stirred overnight. The resulting solution of B8b is then used for the subsequent step.

Step 3:

A solution of B8b in DMF from the preceding step (0.15 M, 1.6 mL, 0.24 mmol) is treated sequentially with compound B8c (Aldrich, 45 mg, 0.28 mmol), DIPEA (0.075 mL, 0.43 mmol) and HATU (110 mg, 0.28 mmol). The reaction is stirred overnight, diluted in AcOH and the product purified directly from this solution by preparative HPLC to give compound 1098.

Example B9

Preparation of Compound 1037

Step 1:

Compound A1a (3.4 g, 26 mmol, Combi Blocks) and B9a (Aldrich, 4.0 g, 26 mmol) and DIPEA (9.1 mL, 52 mmol) are dissolved in DMF (60 mL) and HATU (9.4 g, 25 mmol) is added. The reaction is stirred overnight and then is partitioned between EtOAc and saturated NaHCO$_3$. The organic layer is washed with water and then brine, dried over MgSO$_4$ and concentrated. The residue is purified by Combiflash to give B9b.

Step 2:

Compound B9b (5.3 g, 20 mmol) and Pd(OH)$_2$/C (20% w/w, 2.1 g, 4.0 mmol) are suspended in in EtOH (75 mL). The flask is sealed, evacuated and backfilled with H$_2$ (1 atm) from a balloon. The reaction is stirred overnight and then the flask evacuated and backfilled with N$_2$ (1 atm). The reaction is filtered through Celite and the filtrate is concentrated to give B9c.

Step 3:

Intermediate B9c (1.6 g, 6.9 mmol) and the cyanogen bromide (730 mg, 6.9 mmol) are weighed into a round bottom flask. MeCN (50 mL) and water (12 mL) are added and the mixture is stirred at RT overnight. The reaction is concentrated before being neutralized with saturated NaHCO$_3$. The mixture is filtered and the solid is washed with water and EtOAc. The solid is dried under high vacuum to give B9d. The filtrate is separated and the organic layer is washed with brine, dried over MgSO$_4$, filtered and concentrated to give additional B9d.

Step 4:

Compound 1037 is prepared from B9e (J.W. Pharma) and B9d by analogy to compound 1098, following step 3 from Example B8.

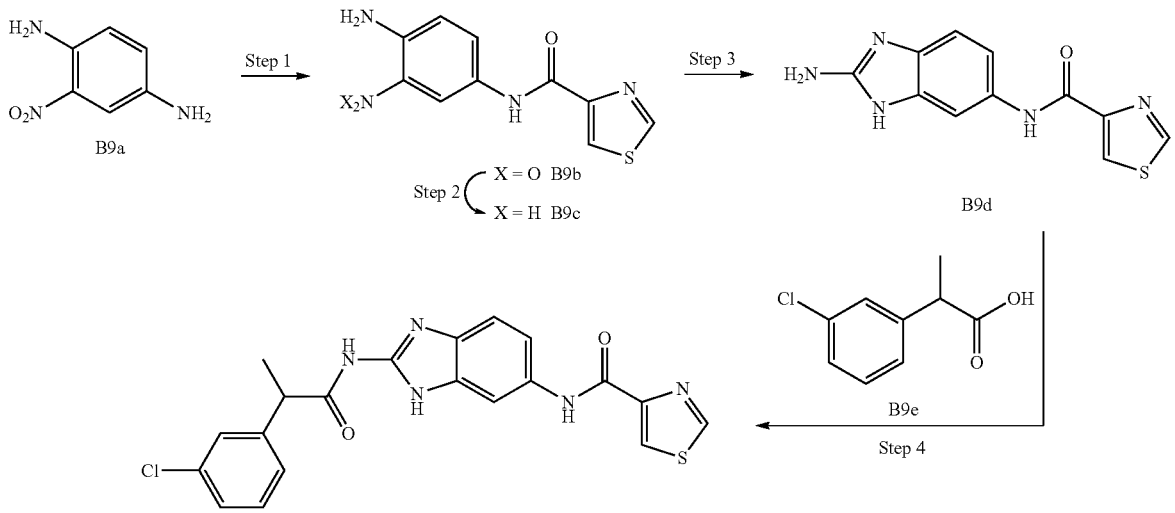

Example B10

Preparation of Compound B9f

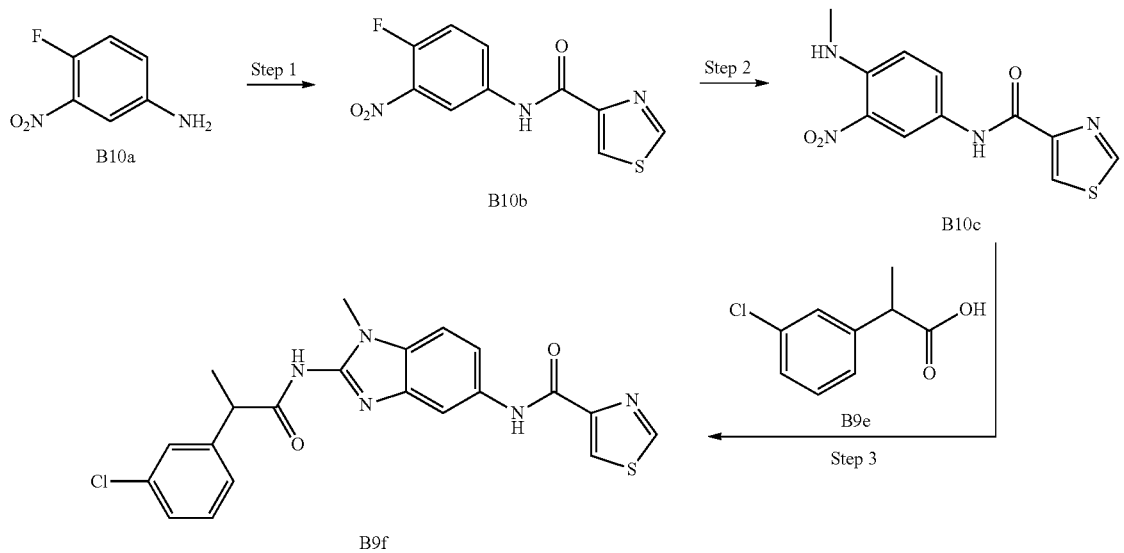

Step 1:

The amine B10a (Aldrich) (1.5 g, 9.6 mmol) is weighed in a round bottom flask and dissolved in DCM (25 mL). Compound A1b (1.5 g, 10 mmol) is added followed by DIPEA (2.5 mL, 14.4 mmol). The reaction is stirred at RT for 1 h and then partitioned between DCM and saturated $NaHCO_3$. The organic layer is washed with water and brine, dried over $MgSO_4$, filtered and concentrated. The residue is purified by Combiflash to give B10b.

Step 2:

Compound B10b (200 mg, 0.8 mmol) and methyl amine hydrochloride (76 mg, 1.1 mmol) are weighed in a microwave vial. DIPEA (0.39 mL, 2.3 mmol) and MeCN (1.5 mL) are added and the reaction is heated to 120° C. under microwave irradiation for 10 min. The reaction mixture is concentrated and partitioned between EtOAc and a saturated aqueous solution of sodium bicarbonate. The organic layer is washed with water and brine, dried over $MgSO_4$, filtered and concentrated to give B10c.

Step 3:

Compound 1121 is prepared from compound B10c by analogy to the preparation of compound 1037 from compound B9b following step 2, 3 and 4 of Example B9.

Example B11

Preparation of Compound 1137

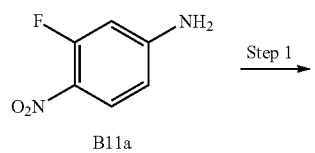

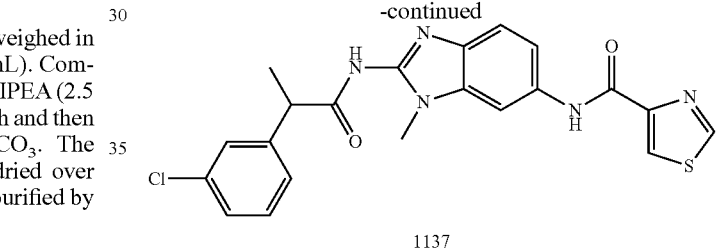

Step 1:

Compound 1137 is prepared from B11a (Oakwood) by analogy to the preparation of compound B9f from compound B10a following step 1, 2 and 3 of Example B10.

Example A

HCMV AD169 CPE Assay

This assay format is a CPE (Cytopathic effect)-based assay that determines the ability of compounds to protect cells against infection with a dye reduction assay (MTS of CellTiter 96® AQueous Non-Radioactive Cell Proliferation Assay from Promega). The conversion of MTS into aqueous, soluble formazan is performed by dehydrogenase enzymes found in metabolically active cells. The quantity of formazan product determined by absorbance at 490 nm is directly proportional to the number of living cells in culture.

Reagents and Material:

| Product | Company | Catalog # | Storage |
| --- | --- | --- | --- |
| MRC-5 cells (Normal human lung fibroblast) | ATCC | CCL-171 | −80° C. |
| HCMV AD169 virus | ATCC | VR-538 | −80° C. |
| D-MEM cell culture medium | Invitrogen | 11995 | 4° C. |

-continued

| Product | Company | Catalog # | Storage |
|---|---|---|---|
| Dulbecco's PBS | Invitrogen | 14190-136 | RT |
| Fetal Bovine Serum | HyClone | SH30396-03 | 4° C. |
| Penicillin/Streptomycin 100X | Invitrogen | 15140 | 4° C. |
| Trypsin-EDTA | Invitrogen | 25300-054 | 4° C. |
| DMSO | VWR (EMD Chemicals) | CAMX1457-6 | RT |
| Clear 384-well assay plates | Greiner | 781182 | RT |
| TopSeal-Adhesive sealing film | PerkinElmer | 6005185 | RT |
| PMS (Phenazine methosulfate) | Sigma | P9625 | −20° C. |
| MTS (3-(4,5-dimethylthiazol-2-yl)-5-(3-carboxymethoxy-phenyl)-2-(4-sulfophenyl)-2H-tetrazolium, inner salt) | Promega | G1111 | −20° C. |

Preparation of Compounds:

Serial dilutions of the DMSO stock compound solution are performed using DMSO in columns 2-11 and 14-23. DMSO alone is present in columns 1, 12, 13 and 24. Four μL of the DMSO serial dilutions is obtained and diluted using 96 μL of D-MEM 5% FBS culture medium to obtain 4% DMSO (7×).

CPE Assay:

To perform the assay, 10 μL of the freshly prepared 4% DMSO serial dilution plate is added to the assay plate containing 40 μL of MRC-5 cells plated the day before (10000 cells per well). Twenty μL of diluted virus is added to columns 2-12 and 14-24 and only D-MEM 5% FBS medium to uninfected control (columns 1 and 13) for a final DMSO concentration of 0.6%. The virus dilution is based on the amount of virus required to obtain a Signal-to-Background of 3-4 (generally between 0.1 and 1 μL of virus stock per well or MOI=0.05). The assay plates are incubated at 37° C. with 5% $CO_2$ for 9 days in order to obtain 100% CPE in infected control without compound (columns 12 and 24). Ten μL of freshly mixed room temperature MTS/PMS (1:20 v/v) is added and the plates are incubated at 37° C. with 5% $CO_2$ for 4-5 h (until signal saturation at 2.3 in the 100% CPE control). The plates are sealed with TopSeal for biosafety and read on the Envision plate reader (Perkin-Elmer) or equivalent at OD 492 nm.

Example B

HCMV AD169-Bac Luciferase Assay

This assay format is a luciferase reporter-based assay that determines the ability of compounds to inhibit the infection by detecting a luciferase signal decrease following the addition of BIGlo substrate (preparation indicated below) directly in the culture media. Mono-oxygenation of luciferin is catalyzed by luciferase in the presence of $Mg_{2+}$, ATP and molecular oxygen. The generation of oxyluciferin is a luminescent reaction that can be detected with the proper platereader. Human Cytomegalovirus AD169-Bac is obtained from Dr. Thomas Shenk at Princeton University (reference paper Yu et al. 2002—J. Virol. 76 (5):2316-2328, herein incorporated by reference) and modified by recombineering to introduce a humanized firefly luciferase gene (Luc2) at the US2-US6 position in the HCMV genome. The virus is expanded in MRC-5 cells.

Reagents and Material:

| Product | Company | Catalog # | Storage |
|---|---|---|---|
| MRC-5 cells (Normal human lung fibroblast) | ATCC | CCL-171 | −80° C. |

-continued

| Product | Company | Catalog # | Storage |
|---|---|---|---|
| HCMV AD169-Bac-Luc2 US2-US6 clone #26 virus | Homemade | | −80° C. |
| D-MEM cell culture medium | Invitrogen | 11995 | 4° C. |
| Dulbecco's PBS | Invitrogen | 14190-136 | RT |
| Fetal Bovine Serum | HyClone | SH30396-03 | 4° C. |
| Penicillin/Streptomycin 100X | Invitrogen | 15140 | 4° C. |
| Trypsin-EDTA | Invitrogen | 25300-054 | 4° C. |
| DMSO | VWR (EMD Chemicals) | CAMX1457-6 | RT |
| Black clear bottom 384-well assay plates | Greiner | 781091 | RT |
| TopSeal-Adhesive sealing film | Perkin Elmer | 6005185 | RT |
| Backing tape white | Perkin Elmer | 6005199 | RT |

For BIGlo Luciferase Buffer:

| Product | Company | Catalog # | Storage |
|---|---|---|---|
| Tricine | Sigma | T0377-250G | RT |
| EDTA 0.5M | Gibco-BRL | 15575-038 | RT |
| NaTPP (Na Triphosphate) | Sigma | T5633-1G | RT |
| MgSO4 | Sigma | M5921-500G | RT |
| ATP | Sigma | A2383-25G | −20° C. |
| Beta-mercaptoethanol | Sigma | M6250-500ml | RT |
| D-Luciferin Potassium salt | GOLD BioTechnology | LUCK-500 or 1G | −20° C. |
| Triton X-100 | Sigma | T9285 | RT |

Final Concentrations:

| | |
|---|---|
| Tricine | 25 mM |
| EDTA | 0.5 mM |
| NaTPP (Na Triphosphate) | 0.54 mM |
| MgSO4 | 16.3 mM |
| **ATP | 1.2 mM |
| **Beta-mercapto. | 56.8 mM |
| **Luciferin | 0.05 mM |
| Triton X-100 | 0.10% | pH 7.8 (adjusted with NaOH 10N)
**add only after pH adjustment
Stored at −80° C.

Preparation of Compounds:

Serial dilutions of the DMSO stock compound solution are performed using DMSO in columns 2-11 and 14-23. DMSO alone is present in columns 1, 12, 13 and 24. Four μL of the DMSO serial dilutions is obtained and diluted using 96 μL of D-MEM 5% FBS culture medium to obtain 4% DMSO (7×).

AD169 Luciferase Assay:

To perform the assay, 7 μL of the freshly prepared 4% DMSO serial dilution plate is added to the assay plate containing 25 μL of MRC-5 cells plated the day before (10000 cells per well). Seventeen μL of diluted virus is added to columns 2-12 and 14-24 and only D-MEM 5% FBS medium to uninfected control (columns 1 and 13) for a final DMSO concentration of 0.6%. The virus dilution is based on the amount of virus required to obtain the highest luciferase signal possible without CPE (generally between 0.05 and 1 μL of virus stock per well or MOI=0.02). The assay plates are incubated at 37° C. with 5% $CO_2$ for 3 days. Fifteen μL of room temperature BIGlo buffer is added to room temperature assay plates also incubated at room temperature for 15 minutes. The plates are sealed with TopSeal for biosafety and the luminescence signal is read on the TopCount plate reader (Perkin-Elmer) or equivalent.

Example C

HCMV AD169 qPCR 96-Well Assay

The hCMV quantitative PCR (qPCR) assay evaluates the ability of a compound to inhibit, directly or indirectly, the replication of hCMV viral DNA during the first 72 h following the infection. Compounds that inhibit either entry or the hCMV polymerase are active in this assay. Compounds are tested in the qPCR assay in 96-well plates, using a 9-point dose-response with 8 compounds for each 96-well plate. The assay was adapted from the method described by Schnepf et al., Rapid determination of antiviral drug susceptibility of human cytomegalovirus by real-time PCR, Antiviral Research 81 (2009) 64-67.

Reagents and Material:

| Product | Company | Catalog # | Storage |
|---|---|---|---|
| MRC-5 cells (Normal human lung fibroblast) | ATCC | CCL-171 | −80° C. |
| HCMV AD169 virus | ATCC | VR-538 | −80° C. |
| D-MEM cell culture medium | Invitrogen | 11995 | 4° C. |
| Dulbecco's PBS | Invitrogen | 14190-136 | RT |
| Fetal Bovine Serum | HyClone | SH30396-03 | 4° C. |
| Trypsin-EDTA | Invitrogen | 25300-054 | 4° C. |
| Penicillin/Streptomycin | Invitrogen | 15140 | 4° C. |
| DMSO | VWR (EMD Chemicals) | CAMX1457-6 | RT |
| Proteinase K >600 mAU/ml | Qiagen | 19131 | RT |
| TaqMan Universal PCR Master mix | AppliedBiosystems | 4326708 | 4° C. |
| TaqMan Fast Advanced Master mix | AppliedBiosystems | 4444558 | 4° C. |
| 384-well clear reaction plate | AppliedBiosystems | 4309849 | RT |
| Optical adhesive covers | AppliedBiosystems | 4311971 | RT |
| Breathable seal | Corning | 80081-122 | RT |
| 384-well microplates | Greiner | 781280 | RT |
| 384-well tissue culture plates | Greiner | 781182 | RT |

For Cell Lysis Buffer:

| Product | Company | Catalog # | Storage |
|---|---|---|---|
| Tris | Gibco-BRL | 15506-017 | RT |
| KCl | Sigma | P9541 | RT |
| $MgCl_2$ | OmniPur | 5980 | RT |
| Tween20 | Sigma | P7949 | RT |
| Nonidet P40 | Sigma | I3021 | RT |

Final Concentrations:

| |
|---|
| 10 mM Tris-HCl pH 8.0 |
| 50 mM KCl |
| 2 mM MgCl2 |
| 0.45% Tween20 |
| 0.45% Nonidet P40 |

Primers and Probes:

qHCMV7=US17 Forward primer, 5' GAA GGT GCA GGT GCC CTG 3' (SEQ ID NO: 1), synthesis by IDT.

qHCMV8=US17 Reverse primer, 5' GTG TCG ACG AAC GAC GTA CG 3' (SEQ ID NO: 2), synthesis by IDT.

qHCMV9=US17 probe, FAM probe with ZEN internal quencher and Iowa Black FQ quencher, 5'-FAM-ACG GTG CTG/ZEN/TAG ACC CGC ATA CAA A-IABkFQ-3' (SEQ ID NO: 3), synthesis by IDT RP8LL=mitochodrial Forward primer, 5' ACC CAC TCC CTC TTA GCC AAT ATT 3' (SEQ ID NO: 4), synthesis by IDT RP9LL=mitochodrial Reverse primer, 5' GTA GGG CTA GGC CCA CCG 3' (SEQ ID NO: 5), synthesis by IDT RP11LL=mitochodrial probe with JOE probe with Iowa Black FQ quencher, 5' JOE-CTA GTC TTT GCC GCC TGC GAA GCA-IABkFQ-3' (SEQ ID NO: 6), synthesis by IDT Preparation of Compounds:

Serial dilutions of the DMSO stock compound solution are performed using DMSO in columns 2-10. DMSO alone is present in columns 1 and 11. Column 12 remains empty. Diluted compounds are further diluted with DMEM 5% FBS cell culture medium.

AD169 qPCR Assay:

To perform the assay, 25 μL of inhibitor dilutions freshly prepared is added to the assay plate containing 50 μL of MRC-5 cells plated the day before (30000 cells per well). In a 9 point dose-response, column 1 contains mock infected cells and serves at negative control, with the appropriate concentration of DMSO, columns 2 to 10 contain compound dilutions and column 11 contains infected cells, with the appropriate concentration of DMSO and serves as the positive control. Column 12 serves for the standard curve in the qPCR process. Twenty-five μL of virus diluted in DMEM 5% FBS medium (to infect at MOI=0.05) is added to columns 2-11 and only D-MEM 5% FBS medium to uninfected control (column 1) for a final DMSO concentration of 0.6%. Incubate plates at 37° C. in 5% $CO_2$ incubator for 3 days. Whole cell lysates are then obtained by adding 100 μL of Cell lysis buffer to each well including freshly added Proteinase K at a ratio of 1:5 (i.e. 200 μL Proteinase K:1000 μL Cell Lysis buffer) and incubating the assay plate at 56° C. for 1 h. Plates are centrifuged at 1300 rpm for 2 minutes to remove any condensation before proceeding with the qPCR.

The cell lysate is carefully pipetted up and down to mix well and diluted 1:40 in $H_2O$ to give a final dilution of 1:80 relative to the 100 μL of lysis buffer that Is added to the cells. 5 μL of diluted lysate is used for the qPCR reaction. An incubation of 5 minutes at 95° C. in a PCR machine is required to inactivate the Proteinase K. The cell lysates can be stored at −20° C. or used to perform qPCR immediately.

Preparation of Standard Curve:

A 81 bp fragment of US17 gene from AD169 is amplified by PCR using primers qHCMV7 and qHCMV8. The PCR product is cloned into pCR4 TOPO vector (Invitrogen) and a clone harboring the insert is selected. A mitochondrial DNA is also added to normalize the HCMV copy number. Serial dilutions of the US17 plasmid and mitochondrial DNA are performed in heat-inactivated lysis buffer at the same dilution as the cell lysates (1:80). Usually, a standard curve ranging from 10E6 to 10E2 copies (per well) is suitable.

A typical qPCR reaction consists of the following:

| | |
|---|---|
| Diluted whole cell lysate | 5 μL |
| TaqMan Universal PCR Master mix | 12.5 μL |
| qHCMV7 and qHCMV8 at 10 μM | 0.5 μL l |
| Probe qHCMV9 at 10 μM | 0.5 μL |
| RP8LL and RP9ll at 10 μM | 0.25 μL |
| Probe RP11LL at 10 μM | 0.25 μL |
| Rox reference dye | 0.5 μL |
| H2O | 5.5 μL |
| 25 μL final volume | |

A qPCR cycle consists of an initial denaturation of DNA and activation of the Taq enzyme at 95° C. for 10 min followed by 45 cycles of 15 seconds at 95° C. and 1 min at 60° C. Fluorescence is measured at each cycle, following the elongation step at 60° C. The reaction, data acquisition and analysis are performed using AppliedBiosystems 7500 Real time PCR system or other suitable real-time PCR system.

All compounds of the invention are tested in at least one of the assays described in Examples A, B and C and show $EC_{50}$ values in the range of 6 µM or less. Representative data is shown below:

| COMPOUND # | $EC_{50}$ (nM) Example A | $EC_{50}$ (nM) Example B | $EC_{50}$ (nM) Example C |
|---|---|---|---|
| 1027 | 2800 | | |
| 1037 | | 69 | |
| 1098 | | 74 | |
| 1122 | 142 | 110 | |
| 1131 | 1519 | 143 | 220 |
| 1137 | 1700 | 1600 | |
| 1143 | 555 | 51 | |
| 1148 | | 658 | |
| 1158 | 250 | 45 | 180 |

Tables of Compounds

The following tables list compounds representative of the invention. Retention times ($t_R$) for each compound are measured using the standard analytical HPLC or UPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions.

All of the compounds in Table 1 are synthesized analogously to the Examples described above. For each compound in the tables, the analogous synthetic route to prepare each compound is identified by Example number. It will be apparent to a skilled person that the analogous synthetic routes may be used, with appropriate modifications, to prepare the compounds of the invention as described herein.

TABLE 1

| Cmpd # | Structure | tR (min) | [M + H]+ | EXAMPLE FOR SYNTHESIS |
|---|---|---|---|---|
| 1006* | 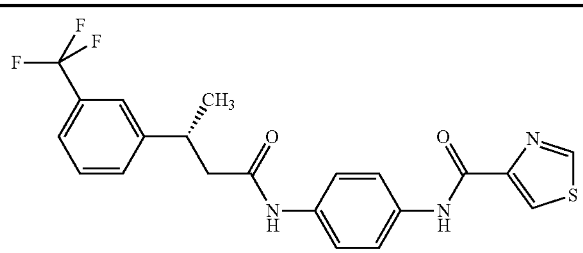 | 1.41 | 434.2 | B1 |
| 1007* | 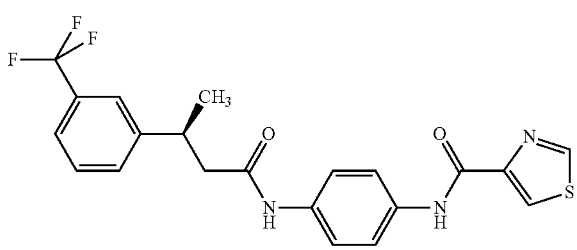 [SMILES: C[C@@H](CC(=O)Nc1ccc(NC(=O)c2cscn2)cc1)c1cccc(C(F)(F)F)c1] | 1.41 | 434.2 | B1 |
| 1019* | 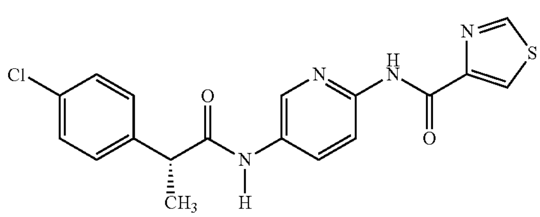 | 1.5 | 387.1 389.0 | B3 |
| 1021* | 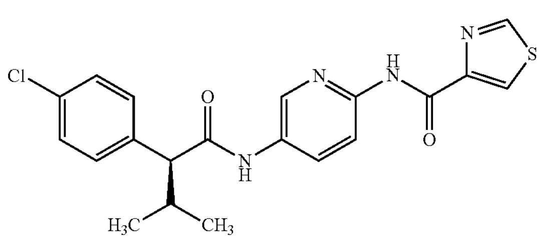 [SMILES: CC(C)[C@H](C(=O)Nc1ccc(NC(=O)c2cscn2)nc1)c1ccc(Cl)cc1] | 1.5 | 415.1 417.1 | B3 |

TABLE 1-continued

| Cmpd # | Structure | tR (min) | [M + H]+ | EXAMPLE FOR SYNTHESIS |
|---|---|---|---|---|
| 1022* | 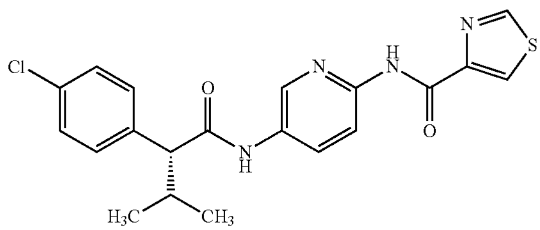 [SMILES: CC(C)[C@@H](C(=O)Nc1ccc(NC(=O)c2cscn2)nc1)c1ccc(Cl)cc1] | 1.5 | 415.1 417.1 | B3 |
| 1024* | 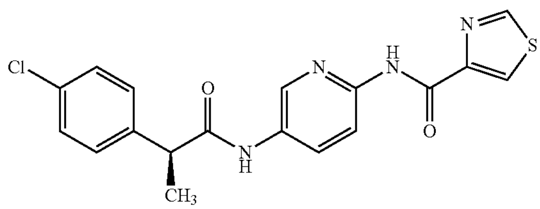 [SMILES: C[C@H](C(=O)Nc1ccc(NC(=O)c2cscn2)nc1)c1ccc(Cl)cc1] | 1.3 | 387.1 389.0 | B3 |
| 1025* | 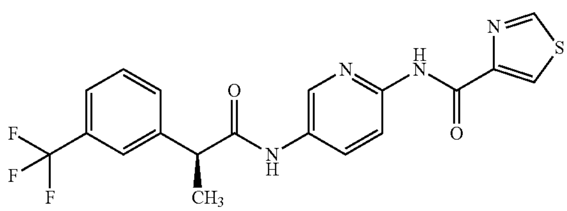 [SMILES: C[C@H](C(=O)Nc1ccc(NC(=O)c2cscn2)nc1)c1cccc(C(F)(F)F)c1] | 1.3 | 421 | B3 |
| 1000 | 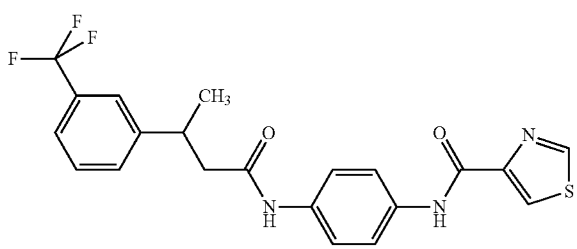 [SMILES: CC(CC(=O)Nc1ccc(NC(=O)c2cscn2)cc1)c1cccc(C(F)(F)F)c1] | 1.39 | 434 | B1 |
| 1001 | 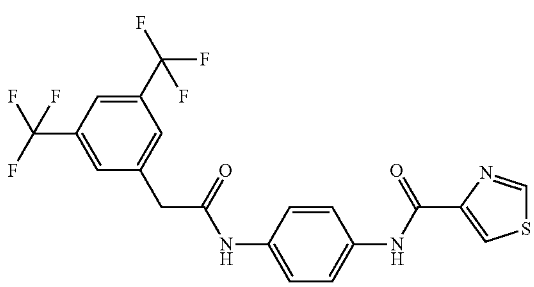 [SMILES: O=C(Cc1cc(C(F)(F)F)cc(C(F)(F)F)c1)Nc1ccc(NC(=O)c2cscn2)cc1] | 1.52 | 474 | B1 |
| 1002 | 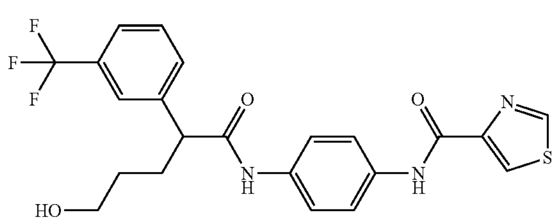 [SMILES: O=C(Nc1ccc(NC(=O)C(CCCO)c2cccc(C(F)(F)F)c2)cc1)c1cscn1] | 1.19 | 464.1 | B1 |

TABLE 1-continued

| Cmpd # | Structure | tR (min) | [M + H]+ | EXAMPLE FOR SYNTHESIS |
|---|---|---|---|---|
| 1003 | 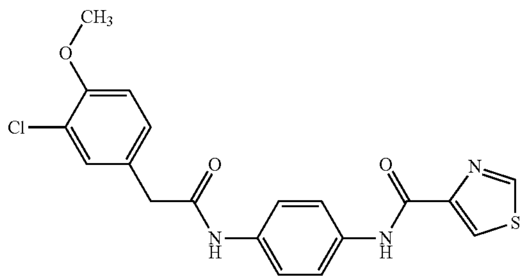 [SMILES: COc1ccc(CC(=O)Nc2ccc(NC(=O)c3cscn3)cc2)cc1Cl] | 1.2 | 402.0 404.0 | B1 |
| 1004 | 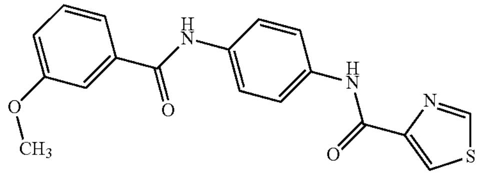 [SMILES: COc1cccc(C(=O)Nc2ccc(NC(=O)c3cscn3)cc2)c1] | 1.61 | 354 | B1 |
| 1005 | 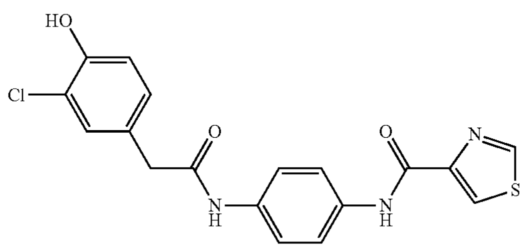 [SMILES: O=C(Cc1ccc(O)c(Cl)c1)Nc1ccc(NC(=O)c2cscn2)cc1] | 0.96 | 387.9 390.0 | B1 |
| 1008 | 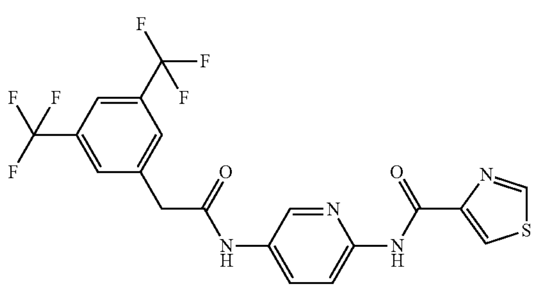 | 1.43 | 475 | B3 |
| 1009 | 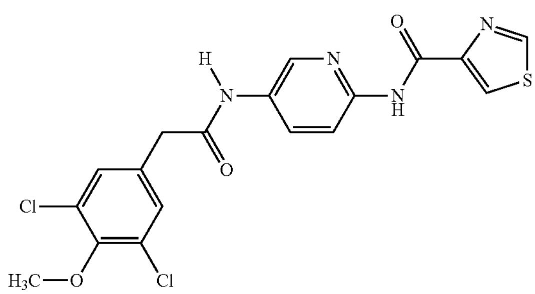 [SMILES: COc1c(Cl)cc(CC(=O)Nc2ccc(NC(=O)c3cscn3)nc2)cc1Cl] | 1.3 | 437.0 439.0 441.1 | B3 |
| 1010 | 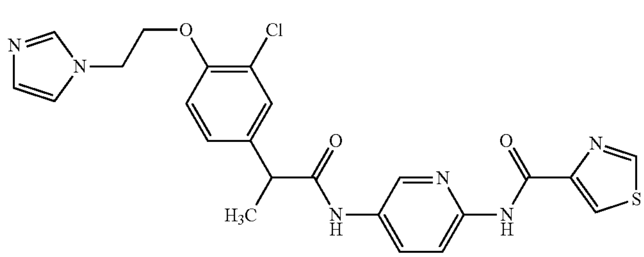 [SMILES: CC(C(=O)Nc1ccc(NC(=O)c2cscn2)nc1)c1ccc(OCCn2ccnc2)c(Cl)c1] | 0.9 | 497.1 499.1 | B3 |

TABLE 1-continued

| Cmpd # | Structure | tR (min) | [M + H]+ | EXAMPLE FOR SYNTHESIS |
|---|---|---|---|---|
| 1011 | 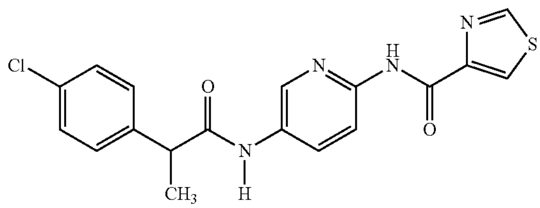 [SMILES: CC(C(=O)Nc1ccc(NC(=O)c2cscn2)nc1)c1ccc(Cl)cc1] | 1.9 | 387.2, 389.2 | B3 |
| 1012 | 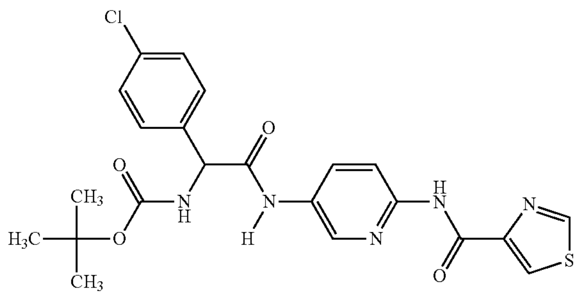 [SMILES: CC(C)(C)OC(=O)NC(C(=O)Nc1ccc(NC(=O)c2cscn2)nc1)c1ccc(Cl)cc1] | 1.4 | 488.1, 490.1 | B3 |
| 1013 | 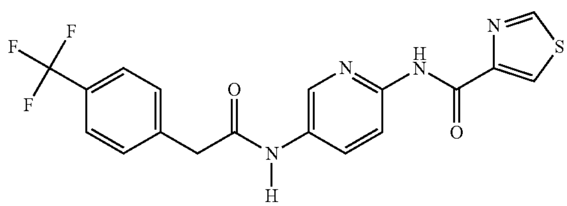 [SMILES: O=C(Cc1ccc(C(F)(F)F)cc1)Nc1ccc(NC(=O)c2cscn2)nc1] | 1.2 | 407.1 | B3 |
| 1014 | 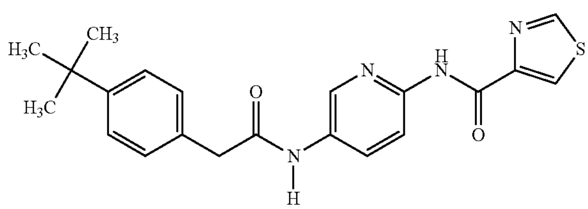 [SMILES: CC(C)(C)c1ccc(CC(=O)Nc2ccc(NC(=O)c3cscn3)nc2)cc1] | 1.4 | 395.2 | B3 |
| 1015 | 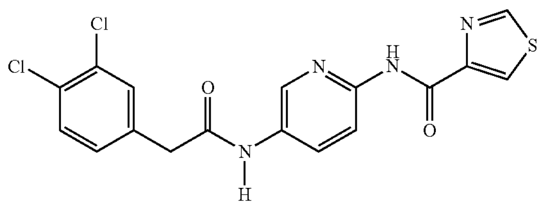 [SMILES: O=C(Cc1ccc(Cl)c(Cl)c1)Nc1ccc(NC(=O)c2cscn2)nc1] | 1.9 | 407.1, 409.1, 411.1 | B3 |
| 1016 | 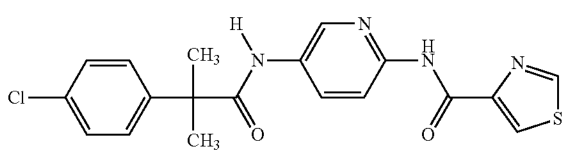 | 1.9 | 401.2, 403.2, 405.2 | B3 |
| 1017 | 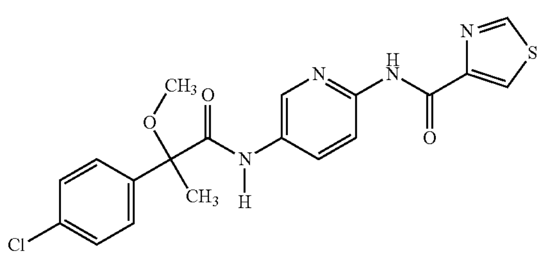 [SMILES: COC(C)(C(=O)Nc1ccc(NC(=O)c2cscn2)nc1)c1ccc(Cl)cc1] | 1.9 | 417.2, 419.2 | B3 |

TABLE 1-continued

| Cmpd # | Structure | tR (min) | [M + H]+ | EXAMPLE FOR SYNTHESIS |
|---|---|---|---|---|
| 1018 | 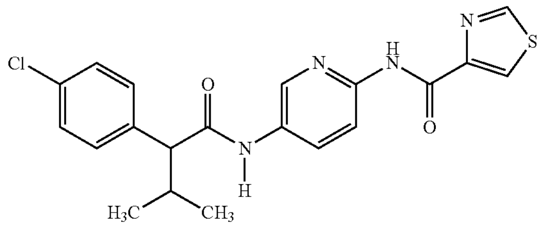 [SMILES: CC(C)C(C(=O)Nc1ccc(NC(=O)c2cscn2)nc1)c1ccc(Cl)cc1] | 1.5 | 415.1 / 417.1 | B3 |
| 1020 | 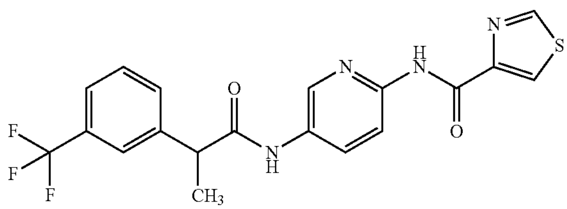 [SMILES: CC(C(=O)Nc1ccc(NC(=O)c2cscn2)nc1)c1cccc(C(F)(F)F)c1] | 1.3 | 421.1 | B3 |
| 1023 | 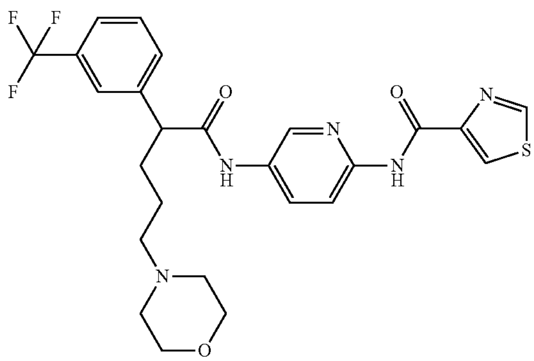 [SMILES: O=C(Nc1ccc(NC(=O)C(CCCN2CCOCC2)c2cccc(C(F)(F)F)c2)cn1)c1cscn1] | 1.02 | 534.2 | B3 |
| 1026 | 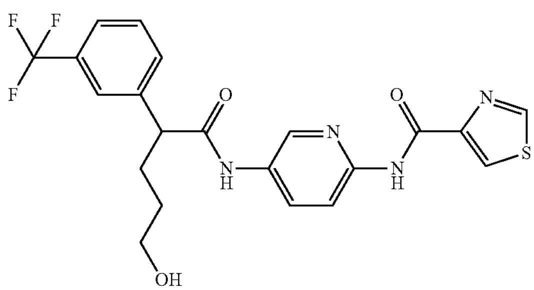 [SMILES: O=C(Nc1ccc(NC(=O)C(CCCO)c2cccc(C(F)(F)F)c2)cn1)c1cscn1] | 1.14 | 465.2 | B3 |
| 1027 | 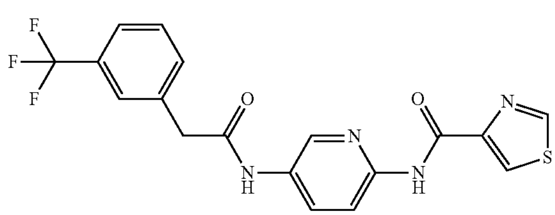 [SMILES: O=C(Cc1cccc(C(F)(F)F)c1)Nc1ccc(NC(=O)c2cscn2)nc1] | 1.2 | 407.1 | B3 |
| 1028 | 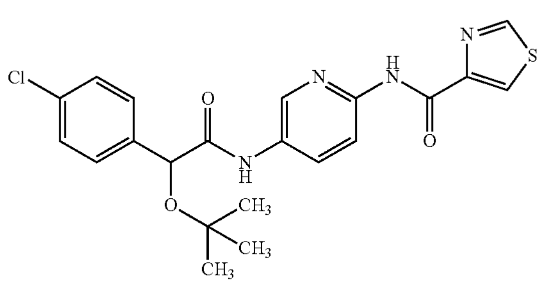 [SMILES: CC(C)(C)OC(C(=O)Nc1ccc(NC(=O)c2cscn2)nc1)c1ccc(Cl)cc1] | 1.5 | 445.2 / 447.1 | B3 |

TABLE 1-continued

| Cmpd # | Structure | tR (min) | [M + H]+ | EXAMPLE FOR SYNTHESIS |
| --- | --- | --- | --- | --- |
| 1029 | 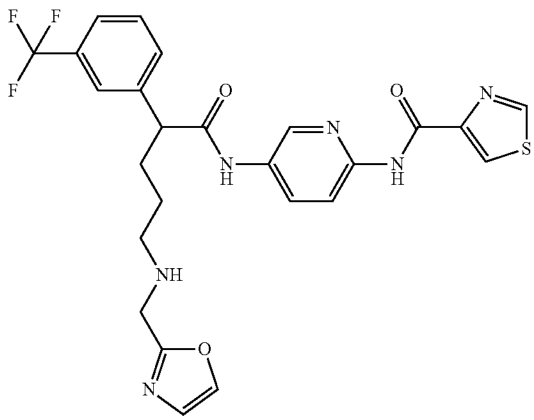 [SMILES: O=C(Nc1ccc(NC(=O)C(CCCNCc2ncco2)c2cccc(C(F)(F)F)c2)cn1)c1cscn1] | 1.02 | 545.2 | B3 |
| 1030 | 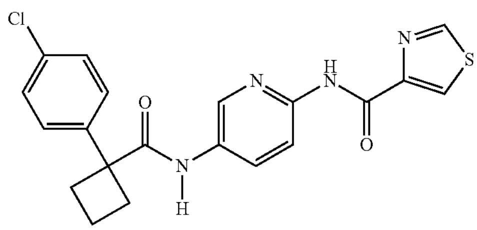 [SMILES: O=C(Nc1ccc(NC(=O)C2(c3ccc(Cl)cc3)CCC2)cn1)c1cscn1] | 1.4 | 413.1<br>415.1 | B3 |
| 1031 | 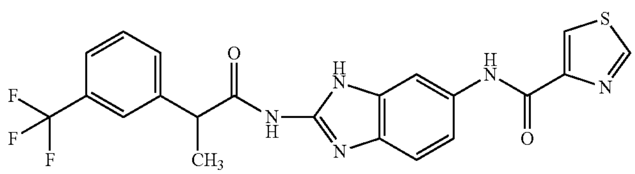 [SMILES: CC(C(=O)Nc1nc2ccc(NC(=O)c3cscn3)cc2[nH]1)c1cccc(C(F)(F)F)c1] | 1.03 | 460 | B9 |
| 1032 | 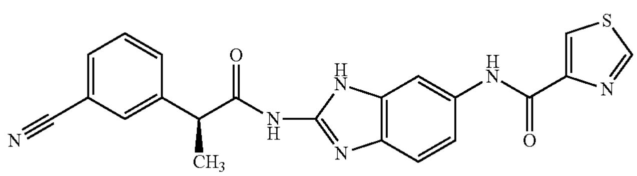 [SMILES: C[C@H](C(=O)Nc1nc2ccc(NC(=O)c3cscn3)cc2[nH]1)c1cccc(C#N)c1] | 1.08 | 417 | B9 |
| 1033 | 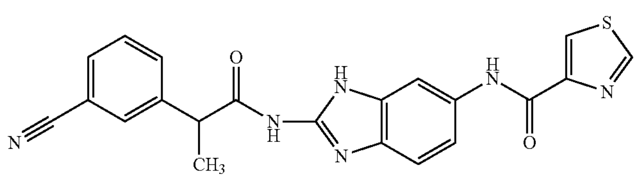 | 1.08 | 417 | B9 |
| 1034 | 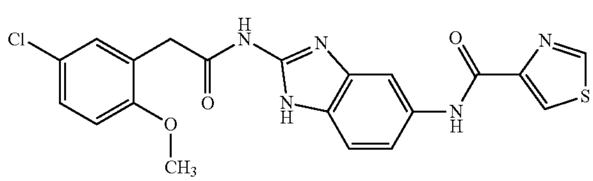 [SMILES: COc1ccc(Cl)cc1CC(=O)Nc1nc2cc(NC(=O)c3cscn3)ccc2[nH]1] | 1.19 | 441.9 | B9 |
| 1035 | 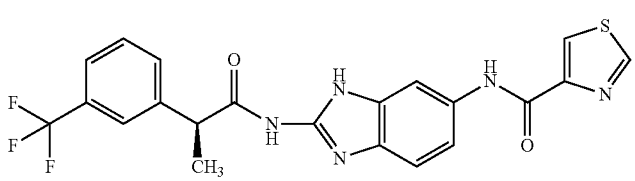 | 1.1 | 460.2 | B9 |

TABLE 1-continued

| Cmpd # | Structure | tR (min) | [M + H]+ | EXAMPLE FOR SYNTHESIS |
| --- | --- | --- | --- | --- |
| 1036 | 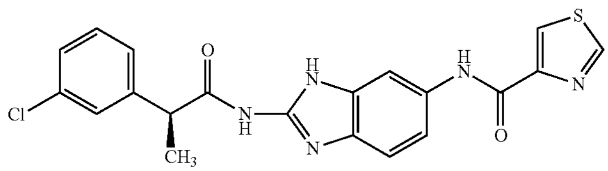 [SMILES: C[C@H](C(=O)Nc1nc2ccc(NC(=O)c3cscn3)cc2[nH]1)c1cccc(Cl)c1] | 1.27 | 426 | B9 |
| 1037 | 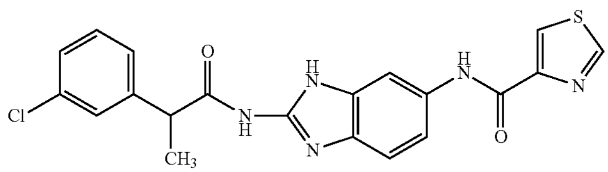 | 1.27 | 425.9 | B9 |
| 1038 | 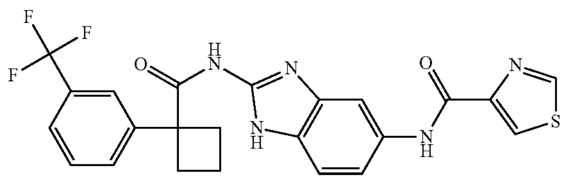 [SMILES: O=C(Nc1ccc2[nH]c(NC(=O)C3(c4cccc(C(F)(F)F)c4)CCC3)nc2c1)c1cscn1] | 1.45 | 486 | B9 |
| 1039 | 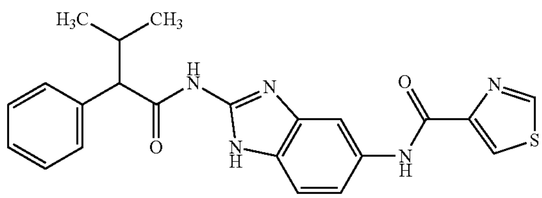 [SMILES: CC(C)C(C(=O)Nc1nc2cc(NC(=O)c3cscn3)ccc2[nH]1)c1ccccc1] | 1.33 | 420 | B9 |
| 1040 | 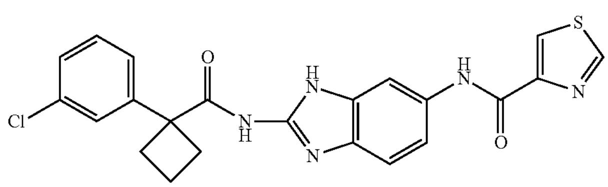 [SMILES: O=C(Nc1ccc2nc(NC(=O)C3(c4cccc(Cl)c4)CCC3)[nH]c2c1)c1cscn1] | 1.4 | 452 | B9 |
| 1041 | 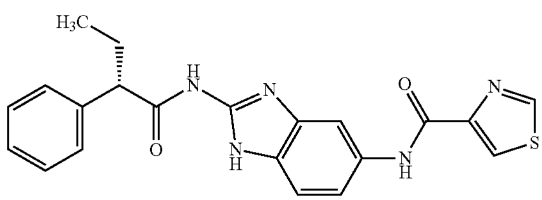 [SMILES: CC[C@H](C(=O)Nc1nc2cc(NC(=O)c3cscn3)ccc2[nH]1)c1ccccc1] | 1.24 | 406 | B9 |
| 1042 | 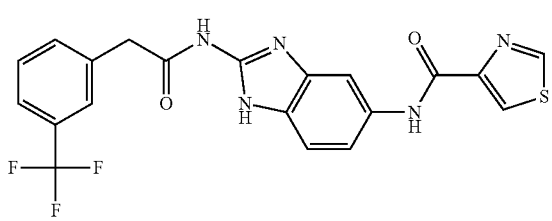 [SMILES: O=C(Cc1cccc(C(F)(F)F)c1)Nc1nc2cc(NC(=O)c3cscn3)ccc2[nH]1] | 1.25 | 446 | B9 |
| 1043 | 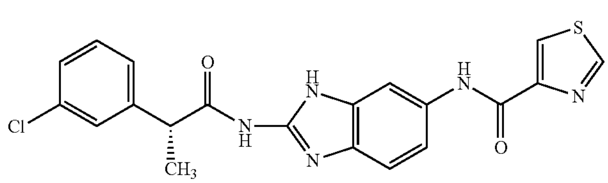 [SMILES: C[C@@H](C(=O)Nc1nc2ccc(NC(=O)c3cscn3)cc2[nH]1)c1cccc(Cl)c1] | 1.27 | 426 | B9 |

TABLE 1-continued

| Cmpd # | Structure | tR (min) | [M + H]+ | EXAMPLE FOR SYNTHESIS |
|---|---|---|---|---|
| 1044 | 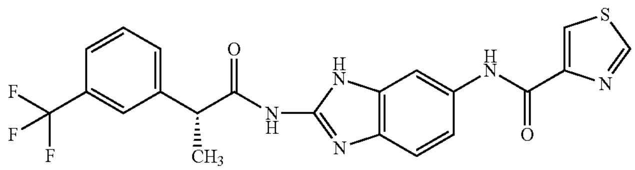 | 1.1 | 460.2 | B9 |
| 1045 | 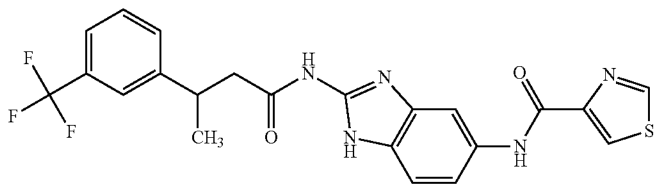 [SMILES: CC(CC(=O)Nc1nc2cc(NC(=O)c3cscn3)ccc2[nH]1)c1cccc(C(F)(F)F)c1] | 1.38 | 474 | B9 |
| 1046 | 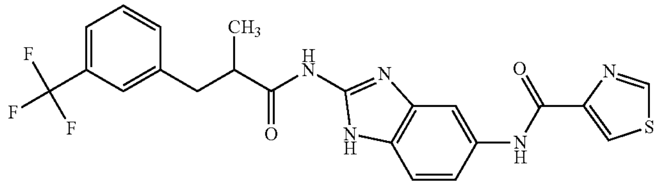 [SMILES: CC(Cc1cccc(C(F)(F)F)c1)C(=O)Nc1nc2cc(NC(=O)c3cscn3)ccc2[nH]1] | 1.37 | 474 | B9 |
| 1047 | 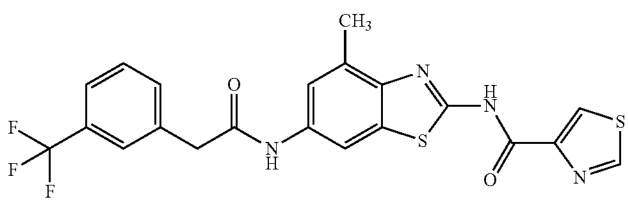 [SMILES: Cc1cc(NC(=O)Cc2cccc(C(F)(F)F)c2)cc2sc(NC(=O)c3cscn3)nc12] | 1.5 | 477.2 | B7 |
| 1048 | 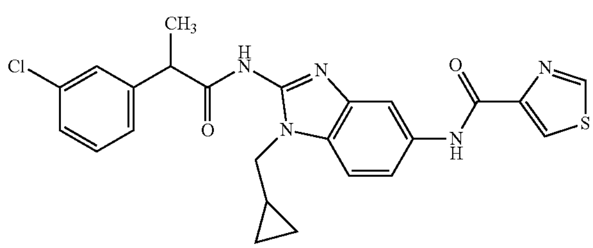 [SMILES: CC(C(=O)Nc1nc2cc(NC(=O)c3cscn3)ccc2n1CC1CC1)c1cccc(Cl)c1] | 1.66 | 480 | B10 |
| 1049 | 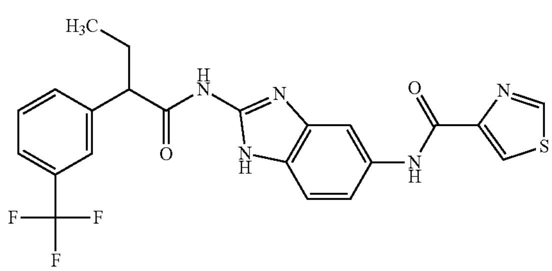 [SMILES: CCC(C(=O)Nc1nc2cc(NC(=O)c3cscn3)ccc2[nH]1)c1cccc(C(F)(F)F)c1] | 1.43 | 474 | B9 |
| 1050 | 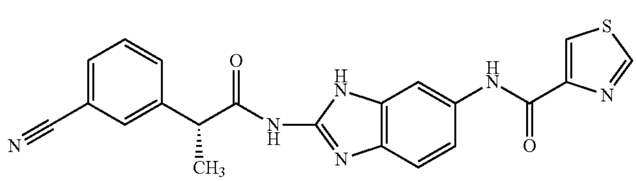 [SMILES: C[C@@H](C(=O)Nc1nc2ccc(NC(=O)c3cscn3)cc2[nH]1)c1cccc(C#N)c1] | 1.08 | 417 | B9 |

TABLE 1-continued

| Cmpd # | Structure | tR (min) | [M + H]+ | EXAMPLE FOR SYNTHESIS |
|---|---|---|---|---|
| 1051 | 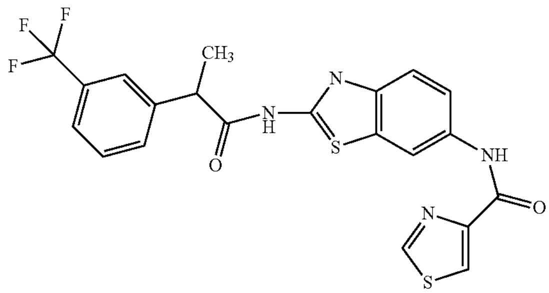 | 1.48 | 477 | B8 |
| 1052 | 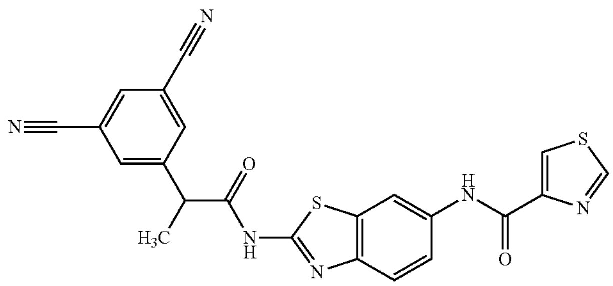 [SMILES: CC(C(=O)Nc1nc2ccc(NC(=O)c3cscn3)cc2s1)c1cc(C#N)cc(C#N)c1] | 1.25 | 457.1 | B8 |
| 1053 | 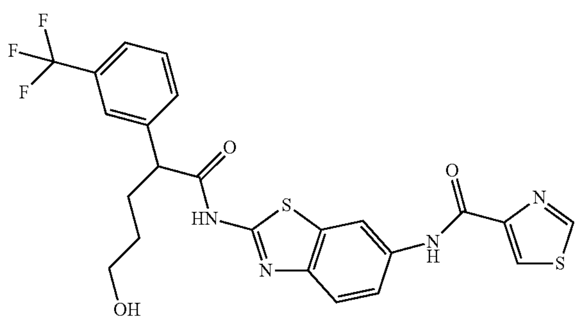 [SMILES: O=C(Nc1ccc2nc(NC(=O)C(CCCO)c3cccc(C(F)(F)F)c3)sc2c1)c1cscn1] | 1.29 | 520.9 | B8 |
| 1054 | 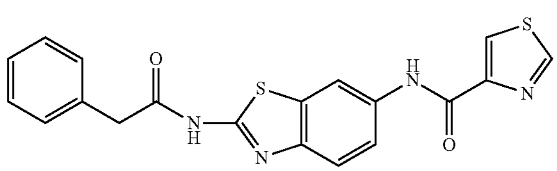 [SMILES: O=C(Cc1ccccc1)Nc1nc2ccc(NC(=O)c3cscn3)cc2s1] | 1.21 | 395 | B8 |
| 1055 | 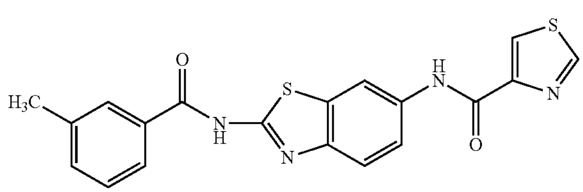 [SMILES: Cc1cccc(C(=O)Nc2nc3ccc(NC(=O)c4cscn4)cc3s2)c1] | 1.34 | 395 | B8 |
| 1056 | 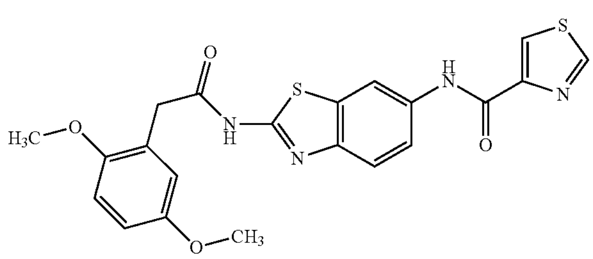 [SMILES: COc1ccc(OC)c(CC(=O)Nc2nc3ccc(NC(=O)c4cscn4)cc3s2)c1] | 1.22 | 455 | B8 |

TABLE 1-continued
| Cmpd # | Structure | tR (min) | [M + H]+ | EXAMPLE FOR SYNTHESIS |
|---|---|---|---|---|
| 1057 | 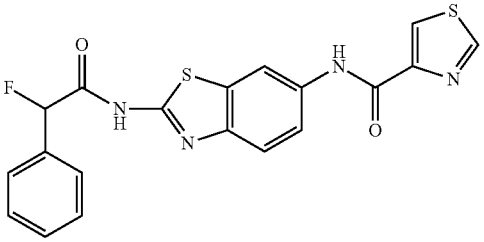 [SMILES: O=C(Nc1ccc2nc(NC(=O)C(F)c3ccccc3)sc2c1)c1cscn1] | 1.25 | 413.1 | B8 |
| 1058 | 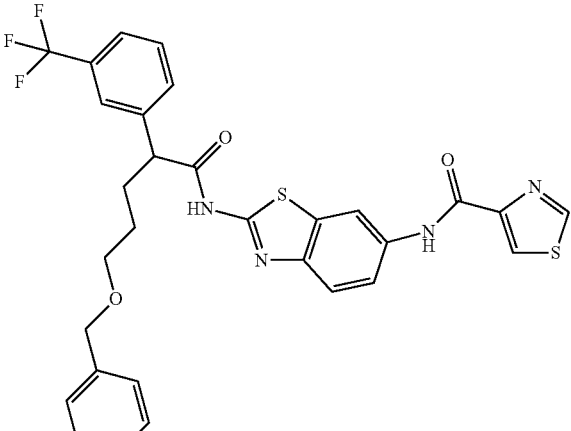 | 1.79 | 610.9 | B8 |
| 1059 | 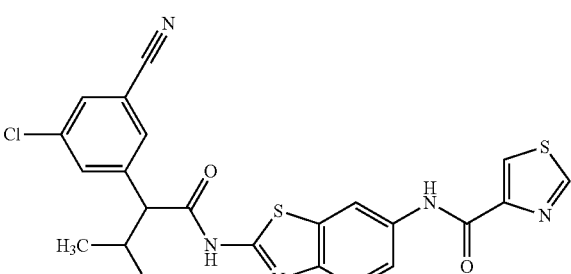 | 1.57 | 495.9 497.9 | B8 |
| 1060 | 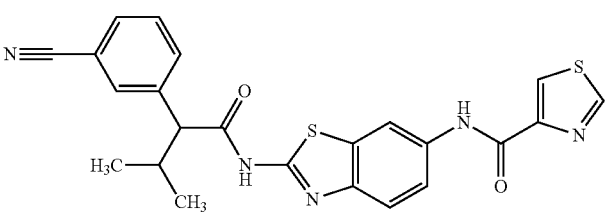 [SMILES: CC(C)C(C(=O)Nc1nc2ccc(NC(=O)c3cscn3)cc2s1)c1cccc(C#N)c1] | 1.42 | 462.2 | B8 |
| 1061 | 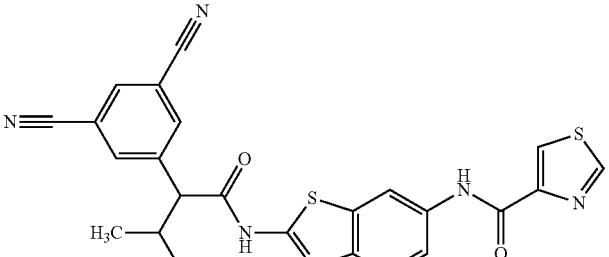 | 1.4 | 487 | B8 |

TABLE 1-continued

| Cmpd # | Structure | tR (min) | [M + H]+ | EXAMPLE FOR SYNTHESIS |
|---|---|---|---|---|
| 1062 | 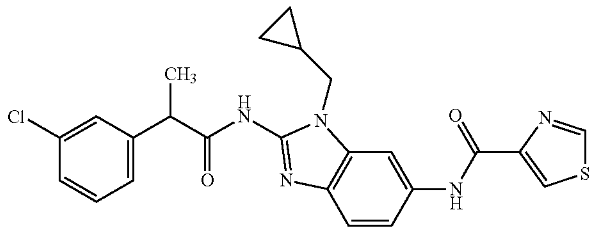 [SMILES: CC(C(=O)Nc1nc2ccc(NC(=O)c3cscn3)cc2n1CC1CC1)c1cccc(Cl)c1] | 1.64 | 480 | B11 |
| 1063 | 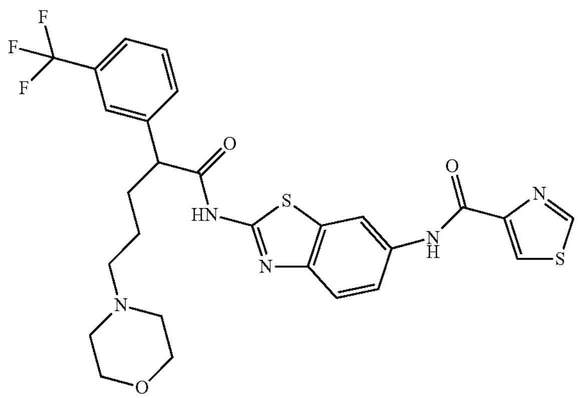 [SMILES: O=C(Nc1ccc2nc(NC(=O)C(CCCN3CCOCC3)c3cccc(C(F)(F)F)c3)sc2c1)c1cscn1] | 1.11 | 590 | B8 |
| 1064 | 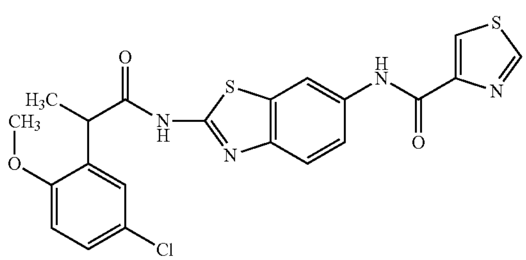 [SMILES: COc1ccc(Cl)cc1C(C)C(=O)Nc1nc2ccc(NC(=O)c3cscn3)cc2s1] | 1.46 | 473.1 475.1 | B8 |
| 1065 | 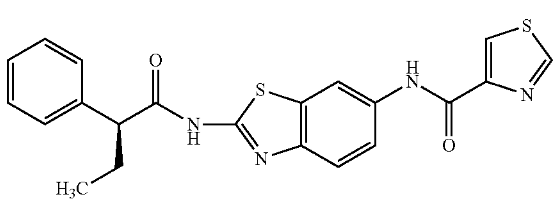 [SMILES: CC[C@H](C(=O)Nc1nc2ccc(NC(=O)c3cscn3)cc2s1)c1ccccc1] | 1.41 | 423.1 | B8 |
| 1066 | 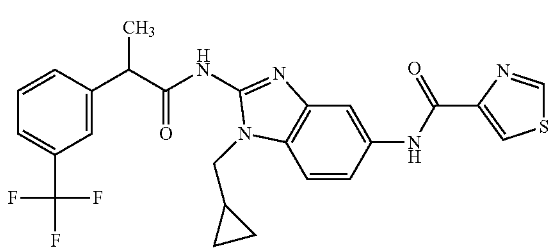 [SMILES: CC(C(=O)Nc1nc2cc(NC(=O)c3cscn3)ccc2n1CC1CC1)c1cccc(C(F)(F)F)c1] | 1.71 | 514.1 | B10 |

TABLE 1-continued

| Cmpd # | Structure | tR (min) | [M + H]+ | EXAMPLE FOR SYNTHESIS |
|---|---|---|---|---|
| 1067 | 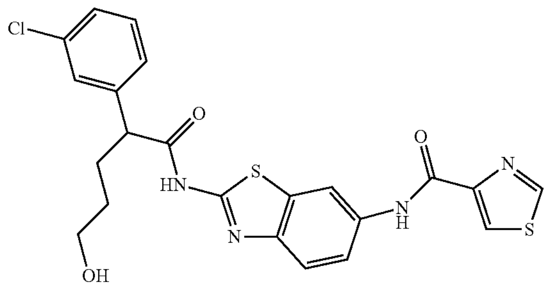 [SMILES: O=C(Nc1ccc2nc(NC(=O)C(CCCO)c3cccc(Cl)c3)sc2c1)c1cscn1] | 1.24 | 487.1 489.1 | B8 |
| 1068 | 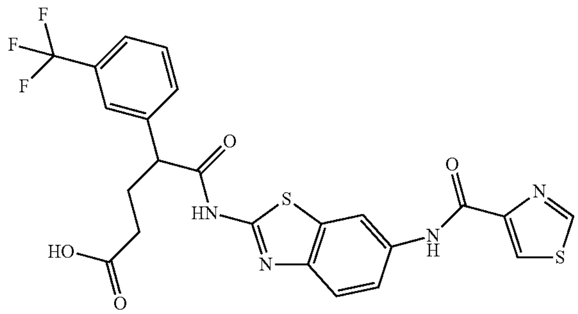 [SMILES: O=C(O)CCC(C(=O)Nc1nc2ccc(NC(=O)c3cscn3)cc2s1)c1cccc(C(F)(F)F)c1] | 1.3 | 535.2 | B8 |
| 1069 | 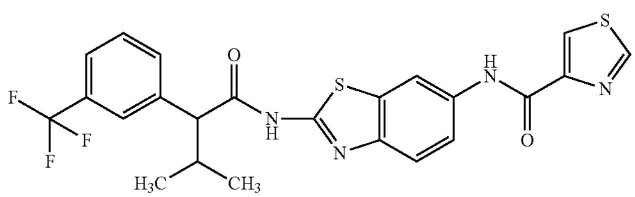 [SMILES: CC(C)C(C(=O)Nc1nc2ccc(NC(=O)c3cscn3)cc2s1)c1cccc(C(F)(F)F)c1] | 1.65 | 505.1 | B8 |
| 1070 | 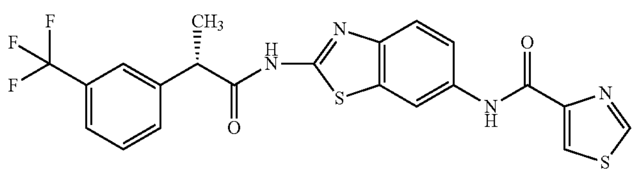 [SMILES: C[C@H](C(=O)Nc1nc2ccc(NC(=O)c3cscn3)cc2s1)c1cccc(C(F)(F)F)c1] | 1.48 | 477.0 | B8 |
| 1071 | 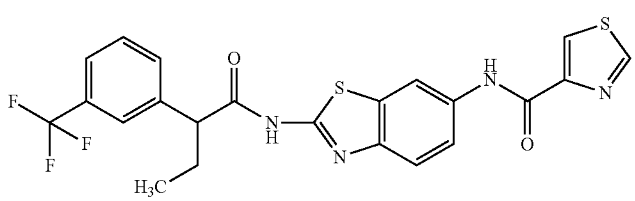 [SMILES: CCC(C(=O)Nc1nc2ccc(NC(=O)c3cscn3)cc2s1)c1cccc(C(F)(F)F)c1] | 1.57 | 491 | B8 |
| 1072 | 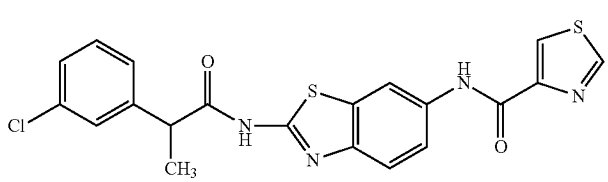 [SMILES: CC(C(=O)Nc1nc2ccc(NC(=O)c3cscn3)cc2s1)c1cccc(Cl)c1] | 1.44 | 442.9 444.9 | B8 |
| 1073 | 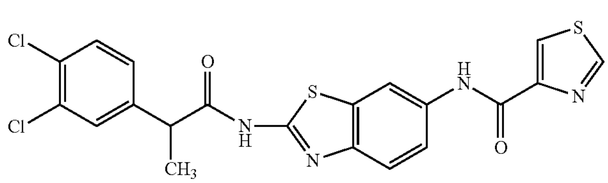 [SMILES: CC(C(=O)Nc1nc2ccc(NC(=O)c3cscn3)cc2s1)c1ccc(Cl)c(Cl)c1] | 1.56 | 476.9 478.9 | B8 |

TABLE 1-continued

| Cmpd # | Structure | tR (min) | [M + H]+ | EXAMPLE FOR SYNTHESIS |
|---|---|---|---|---|
| 1074 | 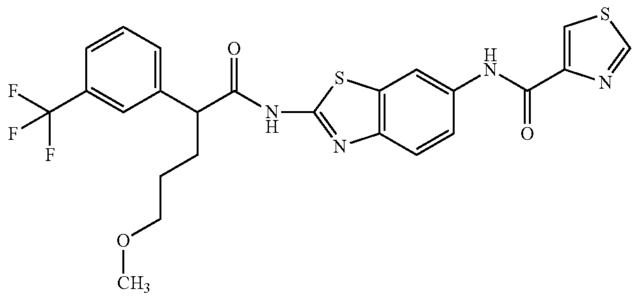 [SMILES: COCCCC(C(=O)Nc1nc2ccc(NC(=O)c3cscn3)cc2s1)c1cccc(C(F)(F)F)c1] | 1.52 | 535.2 | B8 |
| 1075 | 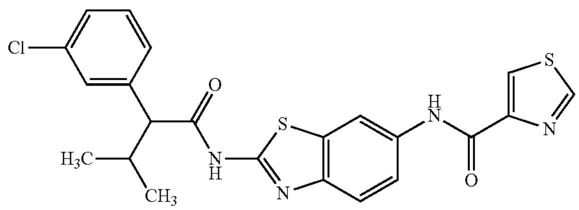 [SMILES: CC(C)C(C(=O)Nc1nc2ccc(NC(=O)c3cscn3)cc2s1)c1cccc(Cl)c1] | 1.62 | 471.2<br>473.2 | B8 |
| 1076 | 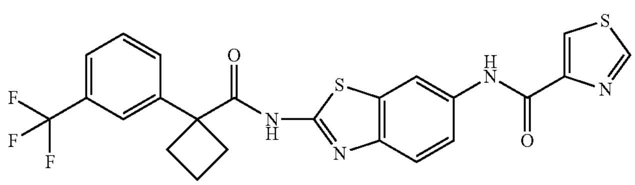 [SMILES: O=C(Nc1ccc2nc(NC(=O)C3(c4cccc(C(F)(F)F)c4)CCC3)sc2c1)c1cscn1] | 1.62 | 502.9 | B8 |
| 1077 | 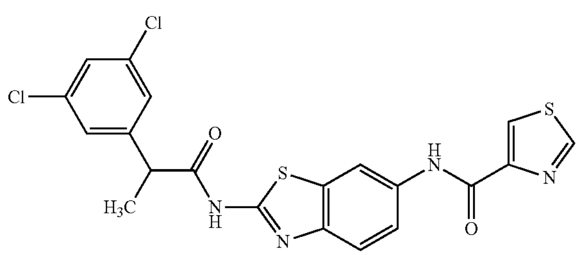 [SMILES: CC(C(=O)Nc1nc2ccc(NC(=O)c3cscn3)cc2s1)c1cc(Cl)cc(Cl)c1] | 1.61 | 475.0<br>476.9<br>478.9 | B8 |
| 1078 | 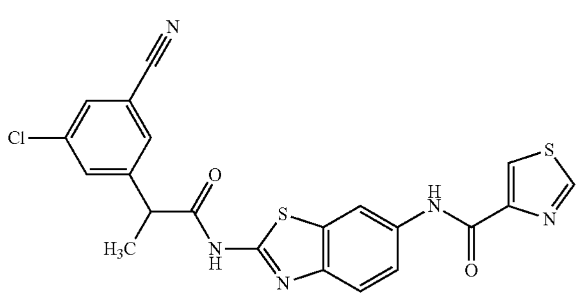 [SMILES: CC(C(=O)Nc1nc2ccc(NC(=O)c3cscn3)cc2s1)c1cc(Cl)cc(C#N)c1] | 1.47 | 468.0<br>470.0 | B8 |

TABLE 1-continued

| Cmpd # | Structure | tR (min) | [M + H]+ | EXAMPLE FOR SYNTHESIS |
|---|---|---|---|---|
| 1079 | 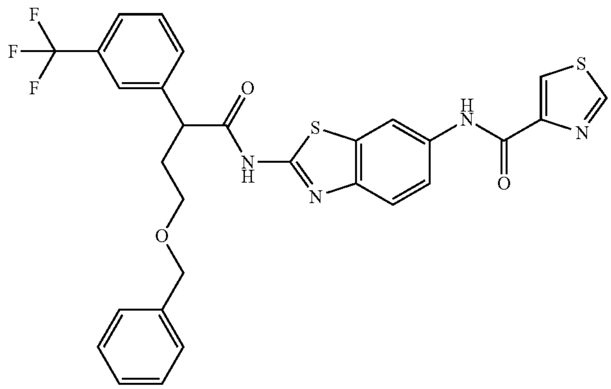 [SMILES: O=C(Nc1ccc2nc(NC(=O)C(CCOCc3ccccc3)c3cccc(C(F)(F)F)c3)sc2c1)c1cscn1] | 1.7 | 596.9 | B8 |
| 1080 | 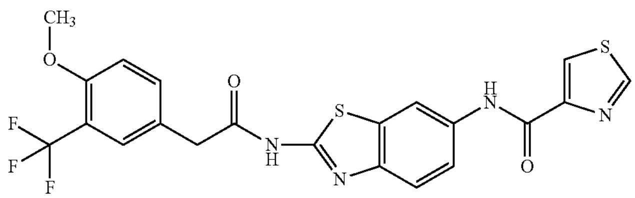 [SMILES: COc1ccc(CC(=O)Nc2nc3ccc(NC(=O)c4cscn4)cc3s2)cc1C(F)(F)F] | 1.36 | 492.9 | B8 |
| 1081 | 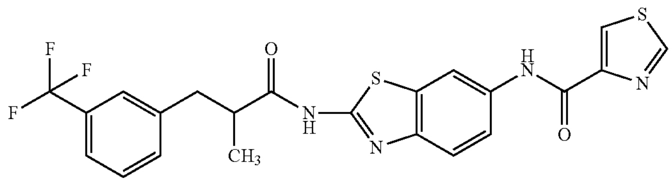 [SMILES: CC(Cc1cccc(C(F)(F)F)c1)C(=O)Nc1nc2ccc(NC(=O)c3cscn3)cc2s1] | 1.5 | 490.9 | B8 |
| 1082 | 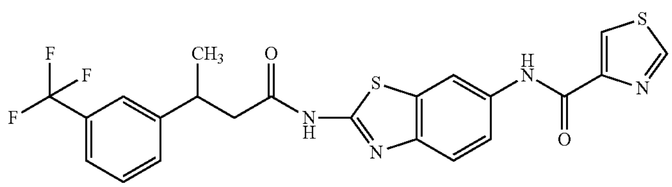 [SMILES: CC(CC(=O)Nc1nc2ccc(NC(=O)c3cscn3)cc2s1)c1cccc(C(F)(F)F)c1] | 1.51 | 491 | B8 |
| 1083 | 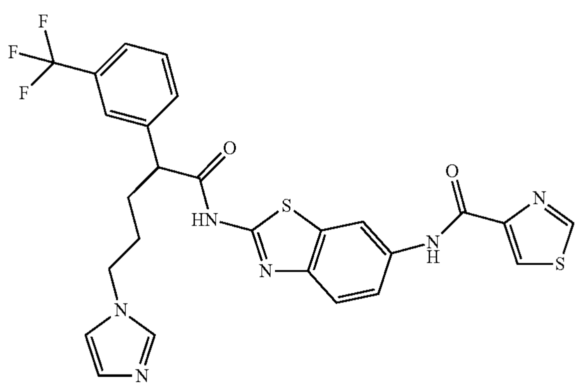 [SMILES: O=C(Nc1ccc2nc(NC(=O)C(CCCn3ccnc3)c3cccc(C(F)(F)F)c3)sc2c1)c1cscn1] | 1.12 | 571 | B8 |
| 1084 | 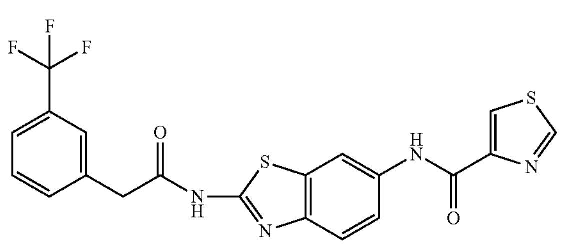 [SMILES: O=C(Cc1cccc(C(F)(F)F)c1)Nc1nc2ccc(NC(=O)c3cscn3)cc2s1] | 1.39 | 463.1 | B8 |

TABLE 1-continued

| Cmpd # | Structure | tR (min) | [M + H]+ | EXAMPLE FOR SYNTHESIS |
|---|---|---|---|---|
| 1085 | 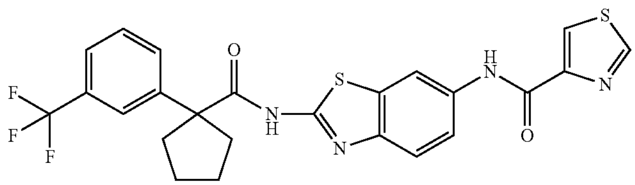 [SMILES: O=C(Nc1ccc2nc(NC(=O)C3(c4cccc(C(F)(F)F)c4)CCCC3)sc2c1)c1cscn1] | 1.72 | 517.2 | B8 |
| 1086 | 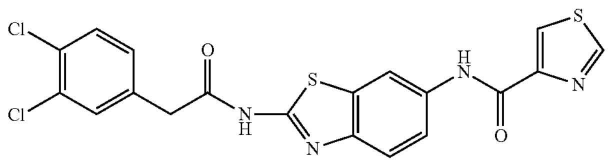 [SMILES: O=C(Cc1ccc(Cl)c(Cl)c1)Nc1nc2ccc(NC(=O)c3cscn3)cc2s1] | 1.45 | 462.8<br>464.9 | B8 |
| 1087 | 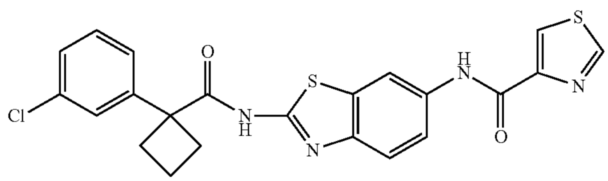 [SMILES: O=C(Nc1ccc2nc(NC(=O)C3(c4cccc(Cl)c4)CCC3)sc2c1)c1cscn1] | 1.59 | 468.9<br>470.9 | B8 |
| 1088 | 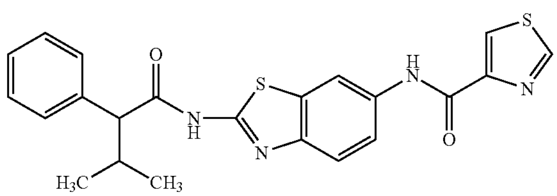 [SMILES: CC(C)C(C(=O)Nc1nc2ccc(NC(=O)c3cscn3)cc2s1)c1ccccc1] | 1.5 | 437 | B8 |
| 1089 | 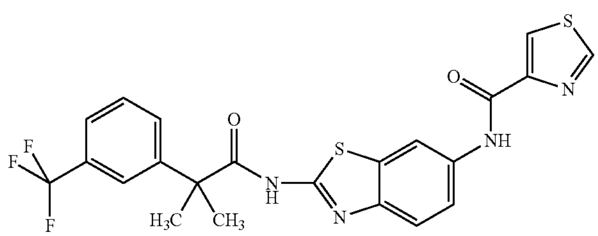 [SMILES: CC(C)(C(=O)Nc1nc2ccc(NC(=O)c3cscn3)cc2s1)c1cccc(C(F)(F)F)c1] | 1.58 | 491.3 | B8 |
| 1090 | 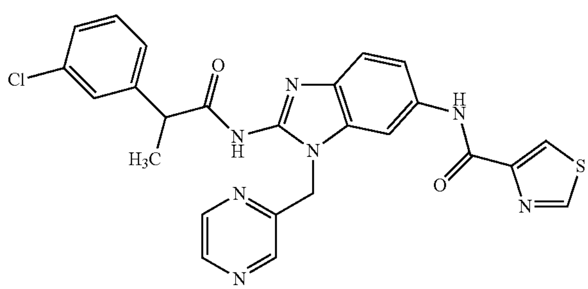 [SMILES: CC(C(=O)Nc1nc2ccc(NC(=O)c3cscn3)cc2n1Cc1cnccn1)c1cccc(Cl)c1] | 1.37 | 518.2 | B11 |
| 1091 | 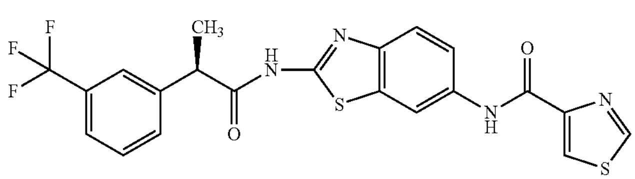 [SMILES: C[C@@H](C(=O)Nc1nc2ccc(NC(=O)c3cscn3)cc2s1)c1cccc(C(F)(F)F)c1] | 1.49 | 477 | B8 |

TABLE 1-continued

| Cmpd # | Structure | tR (min) | [M + H]+ | EXAMPLE FOR SYNTHESIS |
|---|---|---|---|---|
| 1092 | 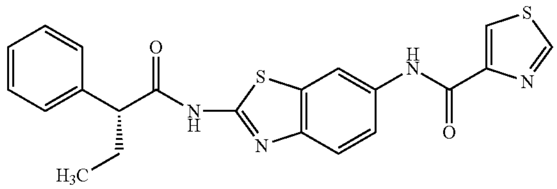 [SMILES: CC[C@@H](C(=O)Nc1nc2ccc(NC(=O)c3cscn3)cc2s1)c1ccccc1] | 1.41 | 423.1 | B8 |
| 1093 | 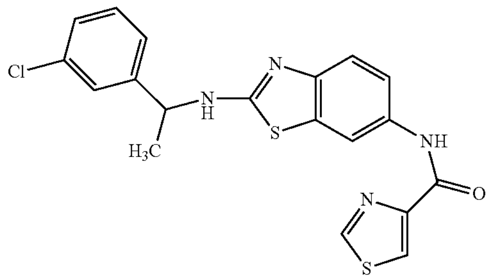 [SMILES: CC(Nc1nc2ccc(NC(=O)c3cscn3)cc2s1)c1cccc(Cl)c1] | 1.14 | 415.0 417.0 | B8 |
| 1094 | 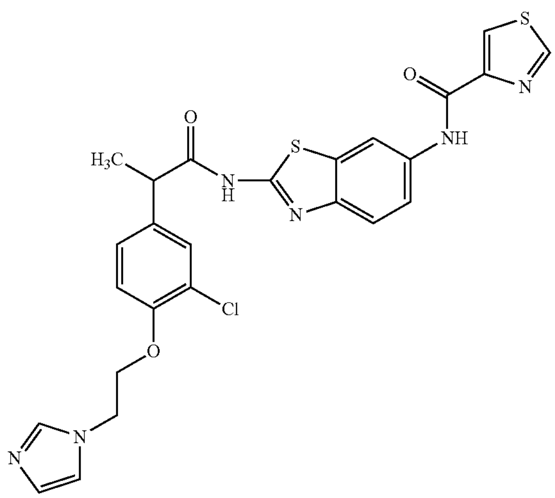 [SMILES: CC(C(=O)Nc1nc2ccc(NC(=O)c3cscn3)cc2s1)c1ccc(OCCn2ccnc2)c(Cl)c1] | 0.99 | 553.3 555.1 | B8 |
| 1095 | 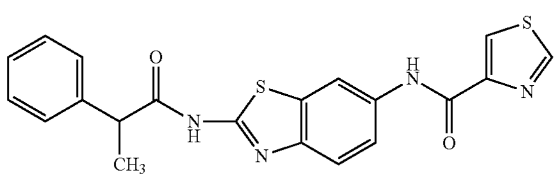 [SMILES: CC(C(=O)Nc1nc2ccc(NC(=O)c3cscn3)cc2s1)c1ccccc1] | 1.31 | 409 | B8 |
| 1096 | 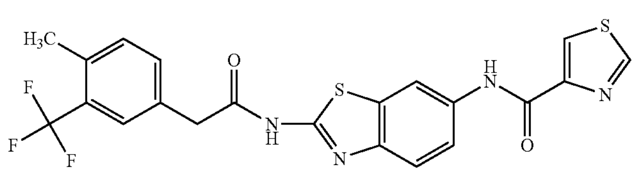 [SMILES: Cc1ccc(CC(=O)Nc2nc3ccc(NC(=O)c4cscn4)cc3s2)cc1C(F)(F)F] | 1.47 | 476.9 | B8 |

TABLE 1-continued

| Cmpd # | Structure | tR (min) | [M + H]+ | EXAMPLE FOR SYNTHESIS |
|---|---|---|---|---|
| 1097 | 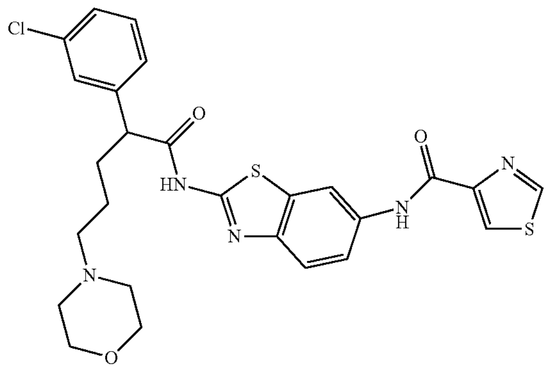 [SMILES: O=C(Nc1ccc2nc(NC(=O)C(CCCN3CCOCC3)c3cccc(Cl)c3)sc2c1)c1cscn1] | 1.05 | 556.2 558.2 | B8 |
| 1098 | 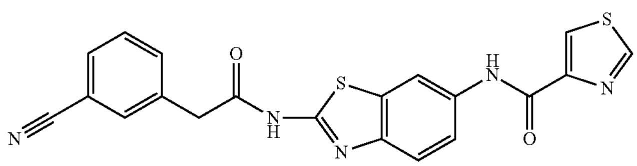 [SMILES: N#Cc1cccc(CC(=O)Nc2nc3ccc(NC(=O)c4cscn4)cc3s2)c1] | 1.15 | 420 | B8 |
| 1099 | 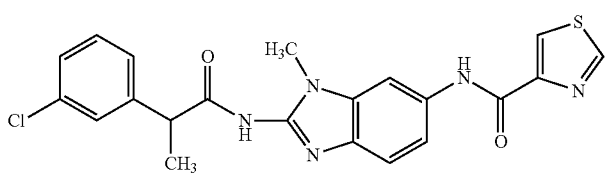 [SMILES: CC(C(=O)Nc1nc2ccc(NC(=O)c3cscn3)cc2n1C)c1cccc(Cl)c1] | 1.38 | 440 | B11 |
| 1100 | 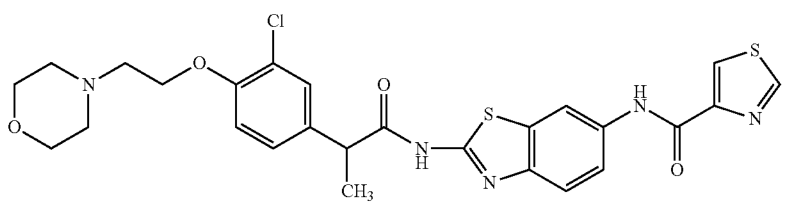 [SMILES: CC(C(=O)Nc1nc2ccc(NC(=O)c3cscn3)cc2s1)c1ccc(OCCN2CCOCC2)c(Cl)c1] | 0.98 | 572.2 574.3 | B8 |
| 1101 | 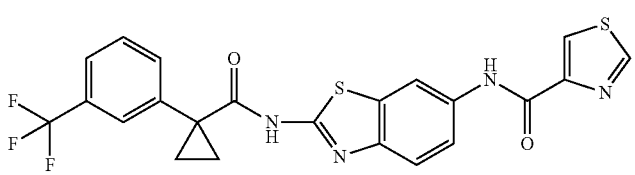 [SMILES: O=C(Nc1ccc2nc(NC(=O)C3(c4cccc(C(F)(F)F)c4)CC3)sc2c1)c1cscn1] | 1.58 | 488.9 | B8 |
| 1102 | 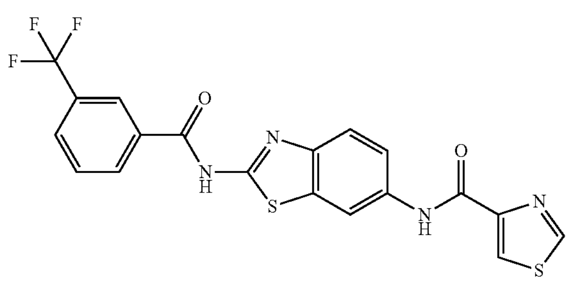 [SMILES: O=C(Nc1nc2ccc(NC(=O)c3cscn3)cc2s1)c1cccc(C(F)(F)F)c1] | 1.44 | 449.1 | B8 |
| 1103 | 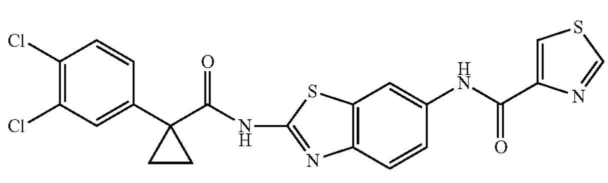 [SMILES: O=C(Nc1ccc2nc(NC(=O)C3(c4ccc(Cl)c(Cl)c4)CC3)sc2c1)c1cscn1] | 1.66 | 488.9 490.9 | B8 |

TABLE 1-continued

| Cmpd # | Structure | tR (min) | [M + H]+ | EXAMPLE FOR SYNTHESIS |
|---|---|---|---|---|
| 1104 | 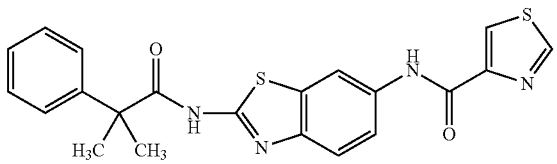 [SMILES: CC(C)(C(=O)Nc1nc2ccc(NC(=O)c3cscn3)cc2s1)c1ccccc1] | 1.43 | 423 | B8 |
| 1105 | 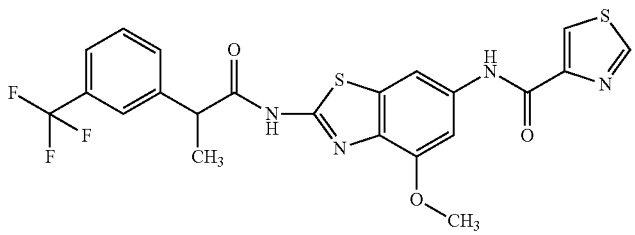 [SMILES: COc1cc(NC(=O)c2cscn2)cc2sc(NC(=O)C(C)c3cccc(C(F)(F)F)c3)nc12] | 1.49 | 507.2 | B8 |
| 1106 | 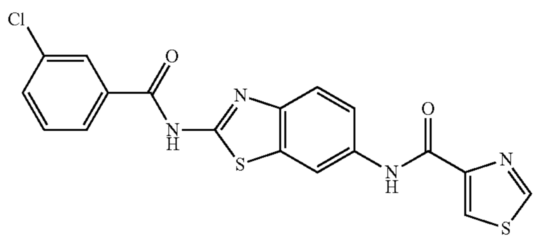 [SMILES: O=C(Nc1nc2ccc(NC(=O)c3cscn3)cc2s1)c1cccc(Cl)c1] | 1.39 | 414.9 417.1 | B8 |
| 1107 | 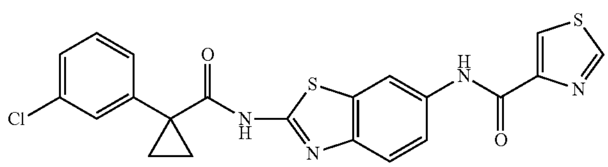 [SMILES: O=C(Nc1ccc2nc(NC(=O)C3(c4cccc(Cl)c4)CC3)sc2c1)c1cscn1] | 1.55 | 455.0 457.0 | B8 |
| 1108 | 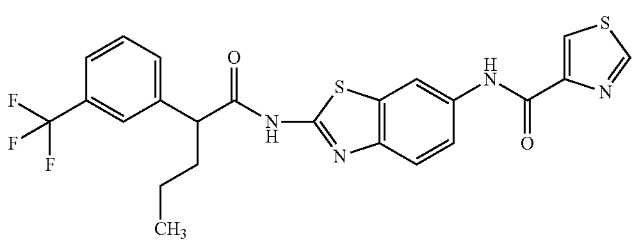 [SMILES: CCCC(C(=O)Nc1nc2ccc(NC(=O)c3cscn3)cc2s1)c1cccc(C(F)(F)F)c1] | 1.67 | 505.2 | B8 |
| 1109 | 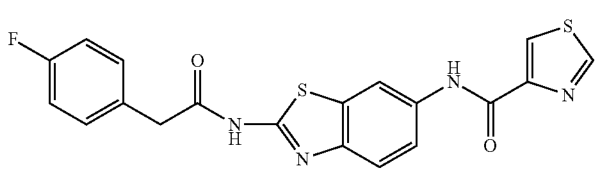 [SMILES: O=C(Cc1ccc(F)cc1)Nc1nc2ccc(NC(=O)c3cscn3)cc2s1] | 1.24 | 413 | B8 |
| 1110 | 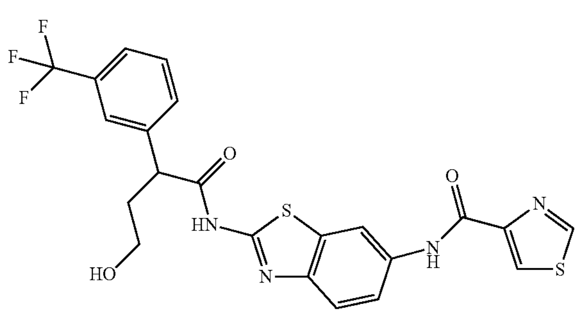 [SMILES: O=C(Nc1ccc2nc(NC(=O)C(CCO)c3cccc(C(F)(F)F)c3)sc2c1)c1cscn1] | 1.28 | 507.2 | B8 |

TABLE 1-continued

| Cmpd # | Structure | tR (min) | [M + H]+ | EXAMPLE FOR SYNTHESIS |
|---|---|---|---|---|
| 1111 | 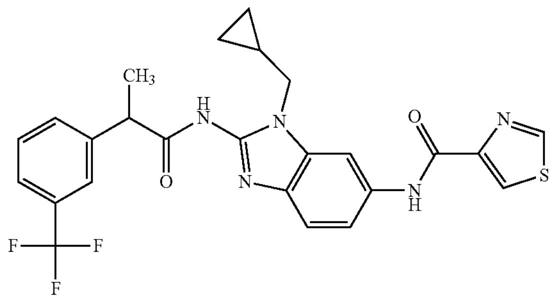 [SMILES: CC(C(=O)Nc1nc2ccc(NC(=O)c3cscn3)cc2n1CC1CC1)c1cccc(C(F)(F)F)c1] | 1.69 | 514.1 | B11 |
| 1112 | 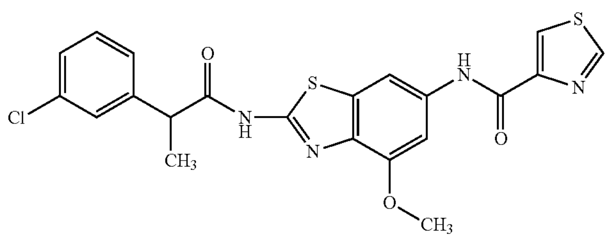 [SMILES: COc1cc(NC(=O)c2cscn2)cc2sc(NC(=O)C(C)c3cccc(Cl)c3)nc12] | 1.45 | 473.2 475.2 | B8 |
| 1113 | 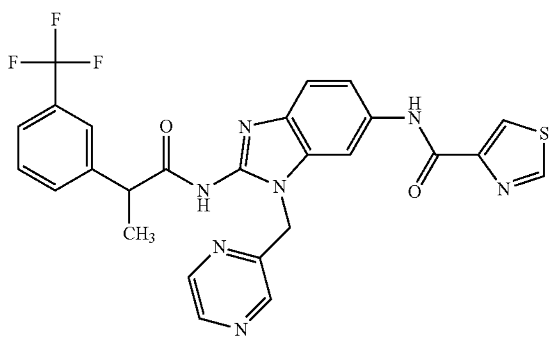 [SMILES: CC(C(=O)Nc1nc2ccc(NC(=O)c3cscn3)cc2n1Cc1cnccn1)c1cccc(C(F)(F)F)c1] | 1.45 | 552.2 | B11 |
| 1114 | 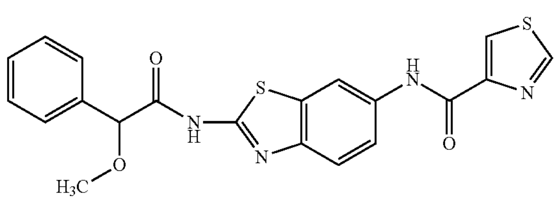 [SMILES: COC(C(=O)Nc1nc2ccc(NC(=O)c3cscn3)cc2s1)c1ccccc1] | 1.28 | 425 | B8 |
| 1115 | 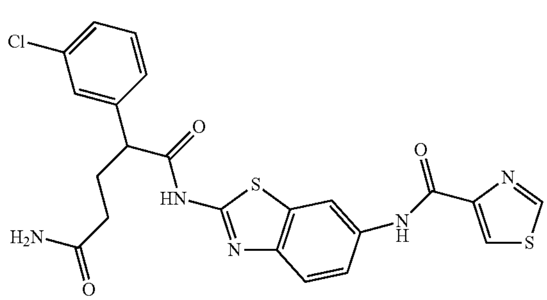 [SMILES: NC(=O)CCC(C(=O)Nc1nc2ccc(NC(=O)c3cscn3)cc2s1)c1cccc(Cl)c1] | 1.14 | 500.3 502.2 | B8 |

TABLE 1-continued

| Cmpd # | Structure | tR (min) | [M + H]+ | EXAMPLE FOR SYNTHESIS |
| --- | --- | --- | --- | --- |
| 1116 | 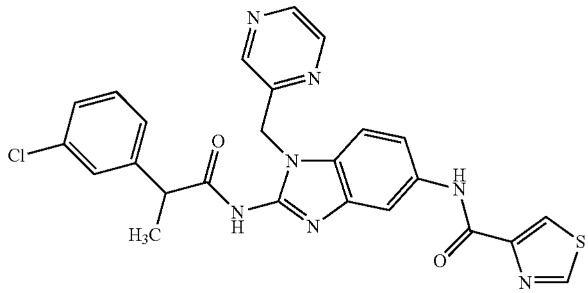 [SMILES: CC(C(=O)Nc1nc2cc(NC(=O)c3cscn3)ccc2n1Cc1cnccn1)c1cccc(Cl)c1] | 1.37 | 518 | B10 |
| 1117 | 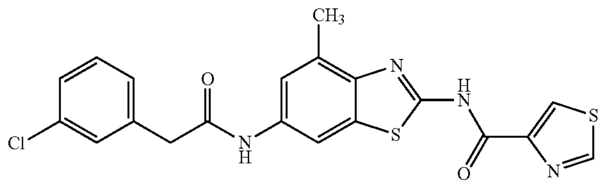 [SMILES: Cc1cc(NC(=O)Cc2cccc(Cl)c2)cc2sc(NC(=O)c3cscn3)nc12] | 1.45 | 443.2 | B7 |
| 1118 | 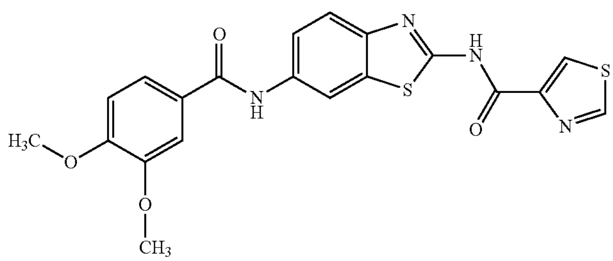 [SMILES: COc1ccc(C(=O)Nc2ccc3nc(NC(=O)c4cscn4)sc3c2)cc1OC] | 1.11 | 441 | B7 |
| 1119 | 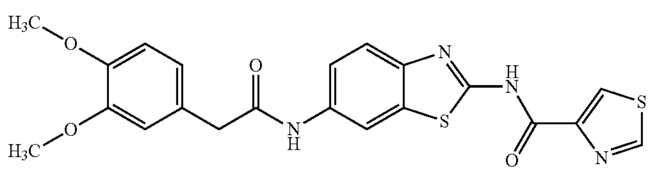 [SMILES: COc1ccc(CC(=O)Nc2ccc3nc(NC(=O)c4cscn4)sc3c2)cc1OC] | 1.08 | 455.1 | B7 |
| 1120 | 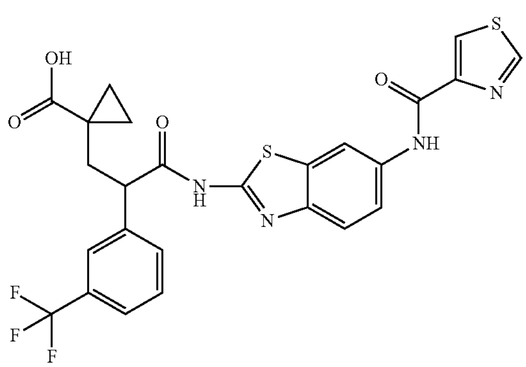 [SMILES: O=C(Nc1ccc2nc(NC(=O)C(CC3(C(=O)O)CC3)c3cccc(C(F)(F)F)c3)sc2c1)c1cscn1] | 1.43 | 561 | B8 |
| 1121 | 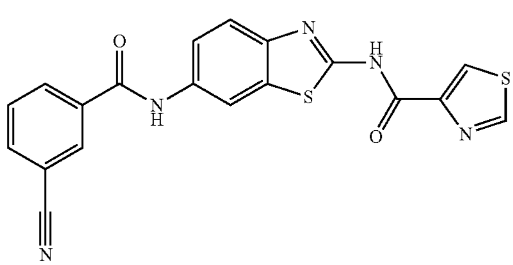 [SMILES: N#Cc1cccc(C(=O)Nc2ccc3nc(NC(=O)c4cscn4)sc3c2)c1] | 1.19 | 406.1 | B7 |

TABLE 1-continued

| Cmpd # | Structure | tR (min) | [M + H]+ | EXAMPLE FOR SYNTHESIS |
|---|---|---|---|---|
| 1122 | 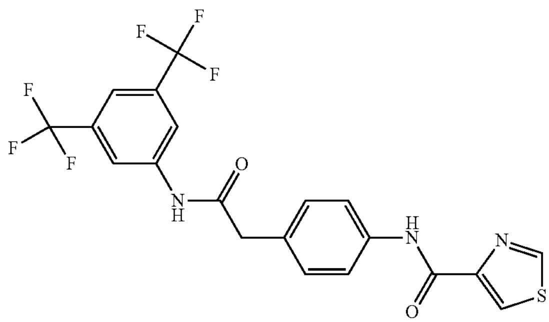 [SMILES: O=C(Cc1ccc(NC(=O)c2cscn2)cc1)Nc1cc(C(F)(F)F)cc(C(F)(F)F)c1] | 1.54 | 474 | B2 |
| 1123 | 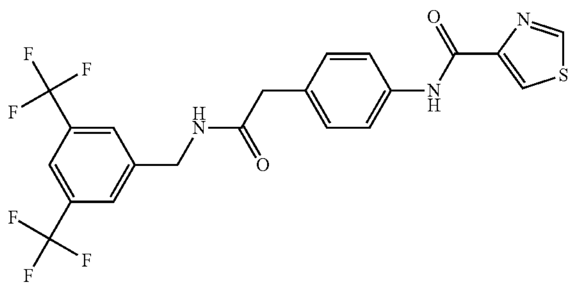 [SMILES: O=C(Cc1ccc(NC(=O)c2cscn2)cc1)NCc1cc(C(F)(F)F)cc(C(F)(F)F)c1] | 1.9 | 488.1 | B2 |
| 1124 | 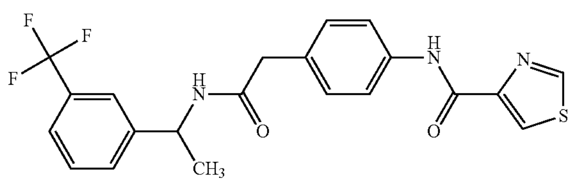 | 1.76 | 434.1 | B2 |
| 1125 | 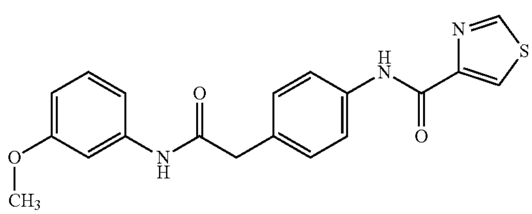 [SMILES: COc1cccc(NC(=O)Cc2ccc(NC(=O)c3cscn3)cc2)c1] | 1.55 | 368.1 | B2 |
| 1126 | 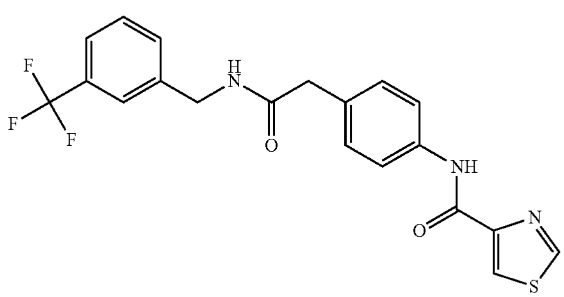 [SMILES: O=C(Cc1ccc(NC(=O)c2cscn2)cc1)NCc1cccc(C(F)(F)F)c1] | 1.71 | 420.2 | B2 |
| 1127 | 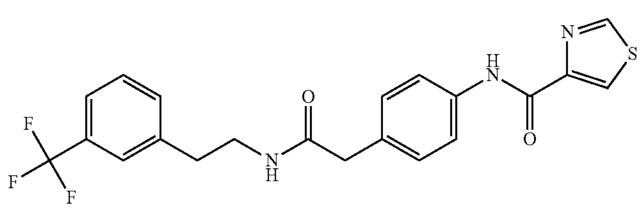 [SMILES: O=C(Cc1ccc(NC(=O)c2cscn2)cc1)NCCc1cccc(C(F)(F)F)c1] | 1.77 | 434.2 | B2 |

TABLE 1-continued

| Cmpd # | Structure | tR (min) | [M + H]+ | EXAMPLE FOR SYNTHESIS |
|---|---|---|---|---|
| 1128 | 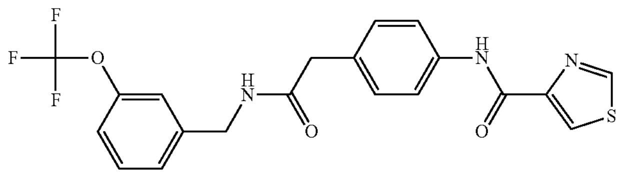 [SMILES: O=C(Cc1ccc(NC(=O)c2cscn2)cc1)NCc1cccc(OC(F)(F)F)c1] | 1.76 | 436.1 | B2 |
| 1129 | 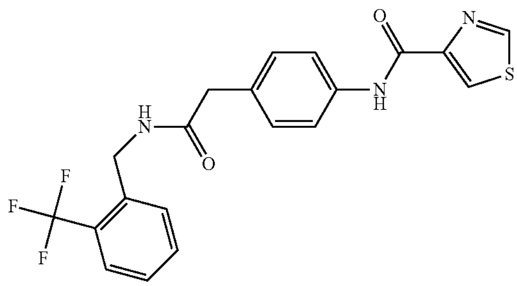 [SMILES: O=C(Cc1ccc(NC(=O)c2cscn2)cc1)NCc1ccccc1C(F)(F)F] | 1.21 | 420.1 | B2 |
| 1130 | 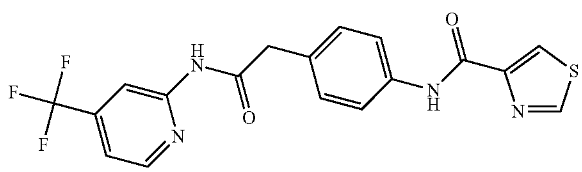 [SMILES: O=C(Cc1ccc(NC(=O)c2cscn2)cc1)Nc1cc(C(F)(F)F)ccn1] | 1.75 | 407.1 | B2 |
| 1131 | 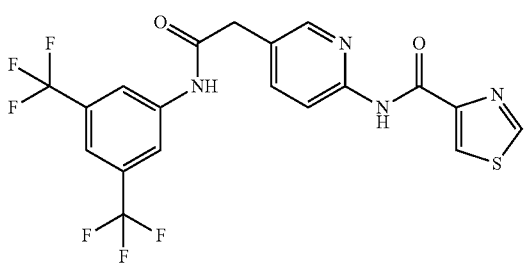 [SMILES: O=C(Cc1ccc(NC(=O)c2cscn2)nc1)Nc1cc(C(F)(F)F)cc(C(F)(F)F)c1] | 1.62 | 475 | B4 |
| 1132 | 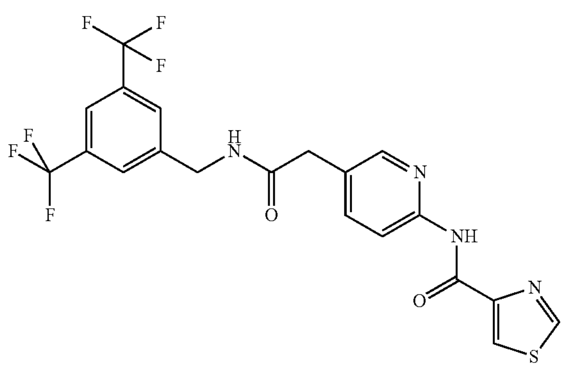 [SMILES: O=C(Cc1ccc(NC(=O)c2cscn2)nc1)NCc1cc(C(F)(F)F)cc(C(F)(F)F)c1] | 1.46 | 489.2 | B4 |
| 1133 | 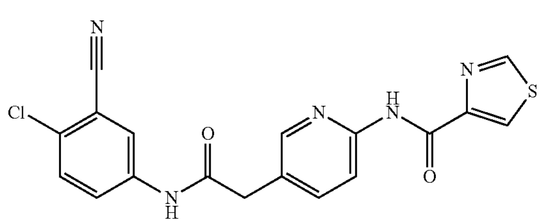 [SMILES: N#Cc1cc(NC(=O)Cc2ccc(NC(=O)c3cscn3)nc2)ccc1Cl] | 1.06 | 398.1 | B4 |

TABLE 1-continued

| Cmpd # | Structure | tR (min) | [M + H]+ | EXAMPLE FOR SYNTHESIS |
|---|---|---|---|---|
| 1134 | 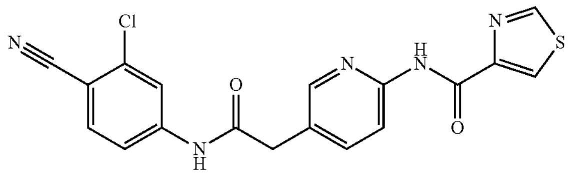 [SMILES: N#Cc1ccc(NC(=O)Cc2ccc(NC(=O)c3cscn3)nc2)cc1Cl] | 1.07 | 398.1 | B4 |
| 1135 | 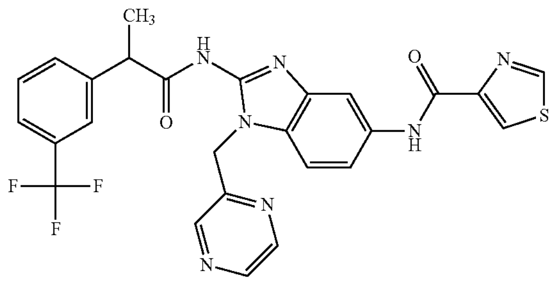 [SMILES: CC(C(=O)Nc1nc2cc(NC(=O)c3cscn3)ccc2n1Cc1cnccn1)c1cccc(C(F)(F)F)c1] | 1.42 | 552 | B10 |
| 1136 | 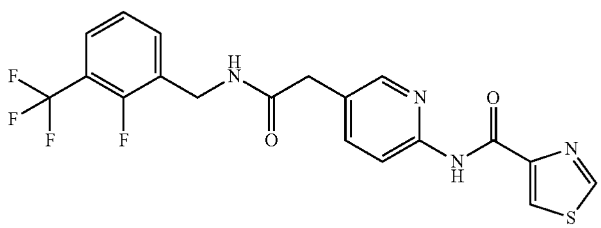 [SMILES: O=C(Cc1ccc(NC(=O)c2cscn2)nc1)NCc1cccc(C(F)(F)F)c1F] | 1.74 | 439.2 | B4 |
| 1137 | 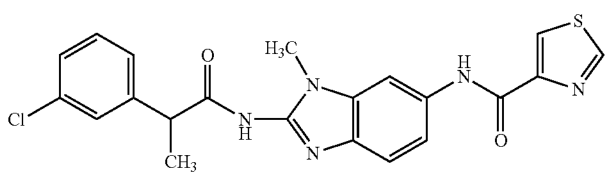 [SMILES: CC(C(=O)Nc1nc2ccc(NC(=O)c3cscn3)cc2n1C)c1cccc(Cl)c1] | 1.38 | 440 | B11 |
| 1138 | 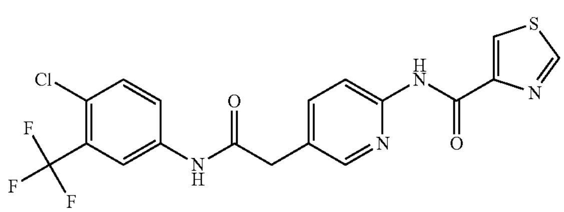 [SMILES: O=C(Cc1ccc(NC(=O)c2cscn2)nc1)Nc1ccc(Cl)c(C(F)(F)F)c1] | 1.96 | 441.2 | B4 |
| 1139 | 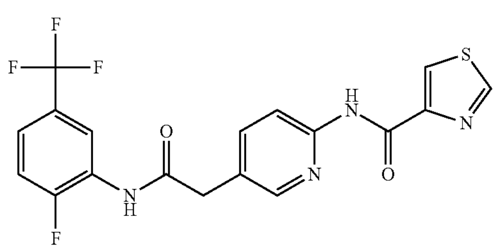 [SMILES: O=C(Cc1ccc(NC(=O)c2cscn2)nc1)Nc1cc(C(F)(F)F)ccc1F] | 1.79 | 425.2 | B4 |
| 1140 | 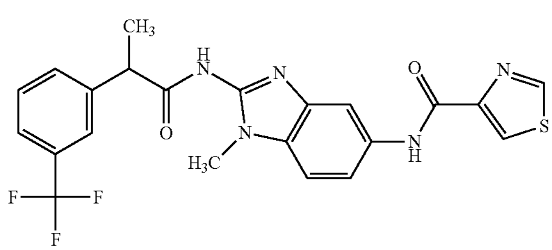 [SMILES: CC(C(=O)Nc1nc2cc(NC(=O)c3cscn3)ccc2n1C)c1cccc(C(F)(F)F)c1] | 1.47 | 474 | B10 |

TABLE 1-continued

| Cmpd # | Structure | tR (min) | [M + H]+ | EXAMPLE FOR SYNTHESIS |
|---|---|---|---|---|
| 1141 | 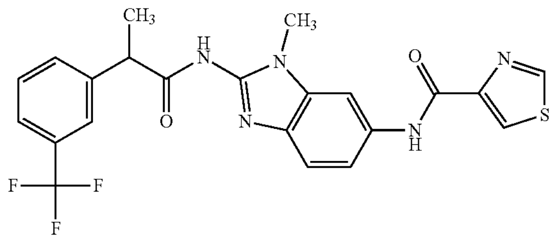 [SMILES: CC(C(=O)Nc1nc2ccc(NC(=O)c3cscn3)cc2n1C)c1cccc(C(F)(F)F)c1] | 1.46 | 474.1 | B11 |
| 1142 | 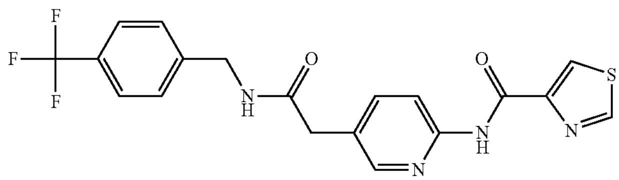 [SMILES: O=C(Cc1ccc(NC(=O)c2cscn2)nc1)NCc1ccc(C(F)(F)F)cc1] | 1.08 | 421.2 | B4 |
| 1143 | 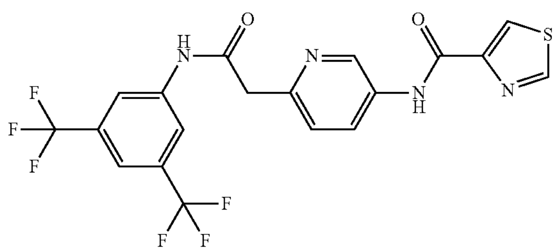 [SMILES: O=C(Cc1ccc(NC(=O)c2cscn2)cn1)Nc1cc(C(F)(F)F)cc(C(F)(F)F)c1] | 1.95 | 475.2 | B6 |
| 1144 | 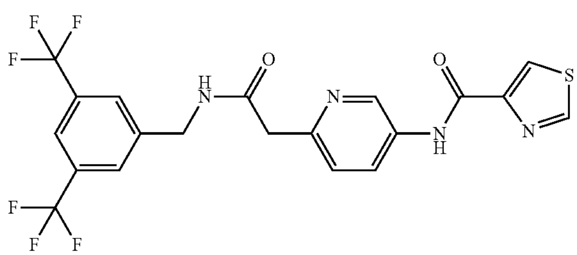 [SMILES: O=C(Cc1ccc(NC(=O)c2cscn2)cn1)NCc1cc(C(F)(F)F)cc(C(F)(F)F)c1] | 1.17 | 489.1 | B6 |
| 1145 | 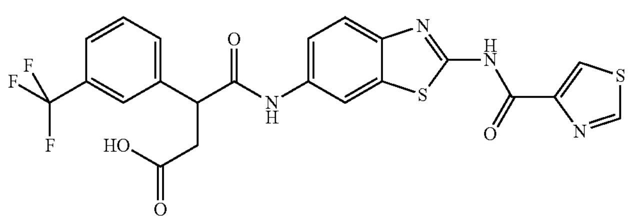 [SMILES: O=C(O)CC(C(=O)Nc1ccc2nc(NC(=O)c3cscn3)sc2c1)c1cccc(C(F)(F)F)c1] | 1.29 | 521.14 | B7 |
| 1146 | 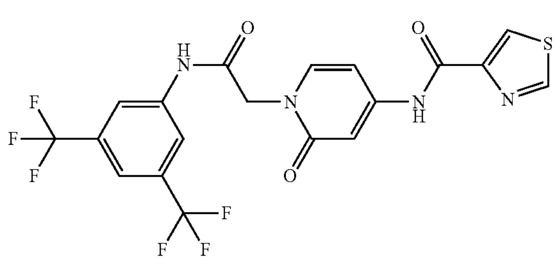 [SMILES: O=C(Cn1ccc(NC(=O)c2cscn2)cc1=O)Nc1cc(C(F)(F)F)cc(C(F)(F)F)c1] | 1.88 | 491.1 | B5 |

TABLE 1-continued

| Cmpd # | Structure | tR (min) | [M + H]+ | EXAMPLE FOR SYNTHESIS |
|---|---|---|---|---|
| 1147 | 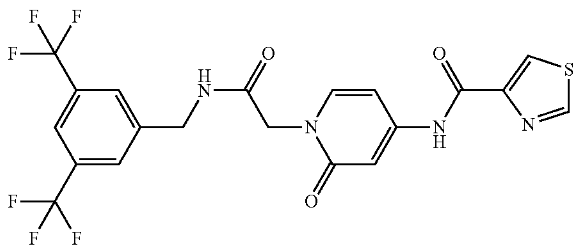 [SMILES: O=C(Cn1ccc(NC(=O)c2cscn2)cc1=O)NCc1cc(C(F)(F)F)cc(C(F)(F)F)c1] | 1.78 | 505.1 | B5 |
| 1148 | 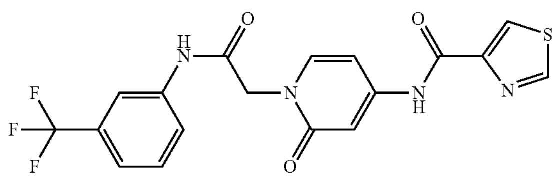 [SMILES: O=C(Cn1ccc(NC(=O)c2cscn2)cc1=O)Nc1cccc(C(F)(F)F)c1] | 1.6 | 423 | B5 |
| 1149 | 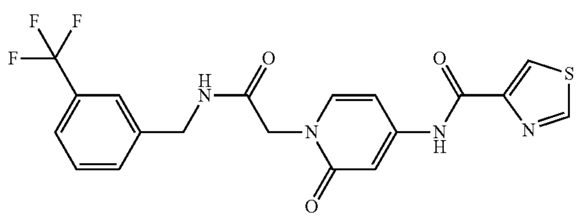 [SMILES: O=C(Cn1ccc(NC(=O)c2cscn2)cc1=O)NCc1cccc(C(F)(F)F)c1] | 1.55 | 437.1 | B5 |
| 1150 | 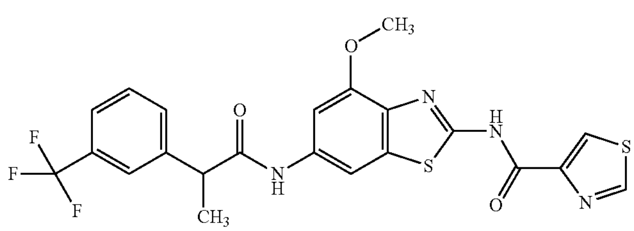 [SMILES: COc1cc(NC(=O)C(C)c2cccc(C(F)(F)F)c2)cc2sc(NC(=O)c3cscn3)nc12] | 1.47 | 507.2 | B7 |
| 1151 | 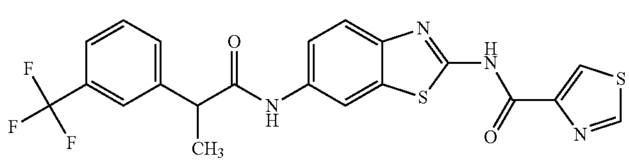 [SMILES: CC(C(=O)Nc1ccc2nc(NC(=O)c3cscn3)sc2c1)c1cccc(C(F)(F)F)c1] | 1.49 | 477 | B7 |
| 1152 | 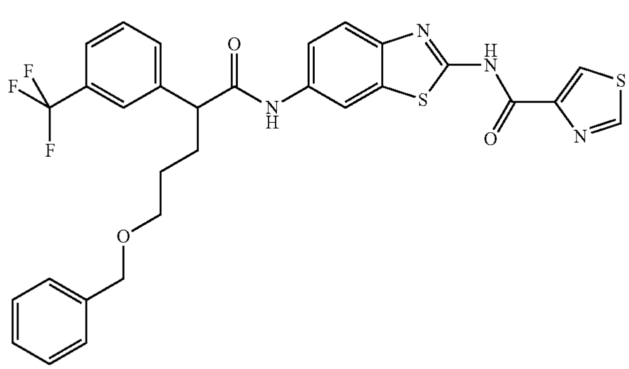 [SMILES: O=C(Nc1nc2ccc(NC(=O)C(CCCOCc3ccccc3)c3cccc(C(F)(F)F)c3)cc2s1)c1cscn1] | 1.8 | 611.26 | B7 |

TABLE 1-continued

| Cmpd # | Structure | tR (min) | [M + H]+ | EXAMPLE FOR SYNTHESIS |
|---|---|---|---|---|
| 1153 | (structure) | 1.42 | 467.94 | B7 |
| 1154 | (structure) | 1.45 | 443.15 | B7 |
| 1155 | (structure) | 1.25 | 458.93 | B7 |
| 1156 | (structure) | 1.46 | 472.93 | B7 |
| 1157 | (structure) | 1.23 | 464 | B7 |
| 1158 | (structure) | 1.39 | 463 | B7 |
| 1159 | (structure) | 1.49 | 491 | B7 |

TABLE 1-continued

| Cmpd # | Structure | tR (min) | [M + H]+ | EXAMPLE FOR SYNTHESIS |
| --- | --- | --- | --- | --- |
| 1160 | 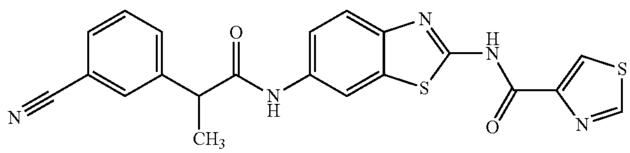 [SMILES: CC(C(=O)Nc1ccc2nc(NC(=O)c3cscn3)sc2c1)c1cccc(C#N)c1] | 1.25 | 433.96 | B7 |
| 1161 | 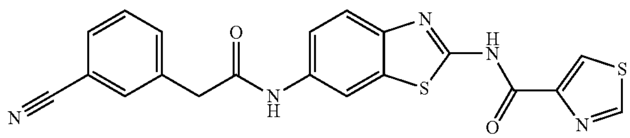 [SMILES: N#Cc1cccc(CC(=O)Nc2ccc3nc(NC(=O)c4cscn4)sc3c2)c1] | 1.16 | 419.99 | B7 |
| 1162 | 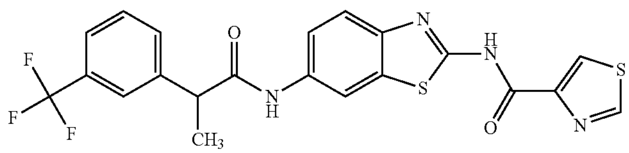 [SMILES: CC(C(=O)Nc1ccc2nc(NC(=O)c3cscn3)sc2c1)c1cccc(C(F)(F)F)c1] | 1.49 | 476.9 | B7 |
| 1163 | 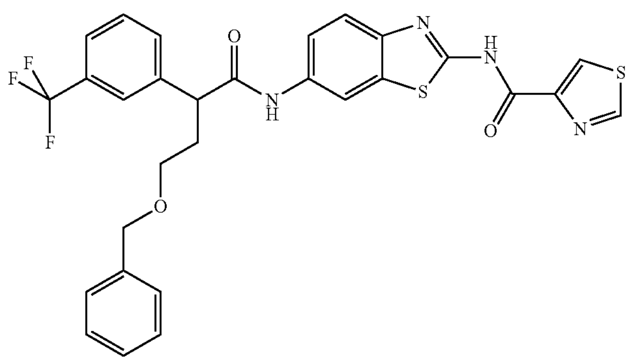 [SMILES: O=C(Nc1nc2ccc(NC(=O)C(CCOCc3ccccc3)c3cccc(C(F)(F)F)c3)cc2s1)c1cscn1] | 1.75 | 597.22 | B7 |
| 1164 | 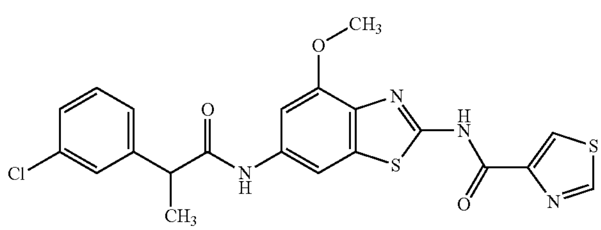 [SMILES: COc1cc(NC(=O)C(C)c2cccc(Cl)c2)cc2sc(NC(=O)c3cscn3)nc12] | 1.43 | 473.17 | B7 |
| 1165 | 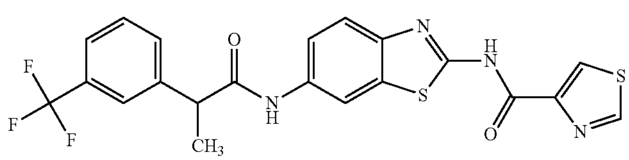 [SMILES: CC(C(=O)Nc1ccc2nc(NC(=O)c3cscn3)sc2c1)c1cccc(C(F)(F)F)c1] | 1.49 | 477 | B7 |
| 1166 | 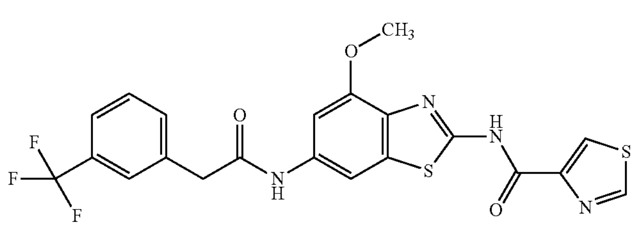 [SMILES: COc1cc(NC(=O)Cc2cccc(C(F)(F)F)c2)cc2sc(NC(=O)c3cscn3)nc12] | 1.38 | 493.17 | B7 |

TABLE 1-continued

| Cmpd # | Structure | tR (min) | [M + H]+ | EXAMPLE FOR SYNTHESIS |
| --- | --- | --- | --- | --- |
| 1167 | 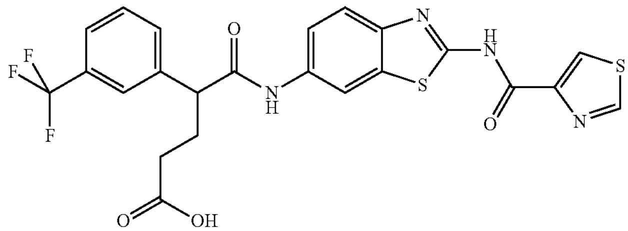 [SMILES: O=C(O)CCC(C(=O)Nc1ccc2nc(NC(=O)c3cscn3)sc2c1)c1cccc(C(F)(F)F)c1] | 1.29 | 535.15 | B7 |
| 1168 | 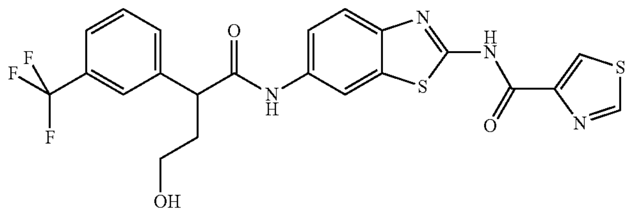 [SMILES: O=C(Nc1nc2ccc(NC(=O)C(CCO)c3cccc(C(F)(F)F)c3)cc2s1)c1cscn1] | 1.27 | 507.19 | B7 |
| 1169 | 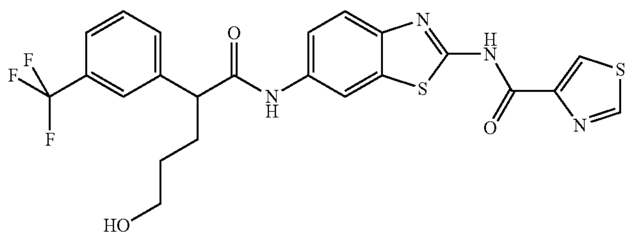 [SMILES: O=C(Nc1nc2ccc(NC(=O)C(CCCO)c3cccc(C(F)(F)F)c3)cc2s1)c1cscn1] | 1.28 | 521.19 | B7 |
| 1170 | 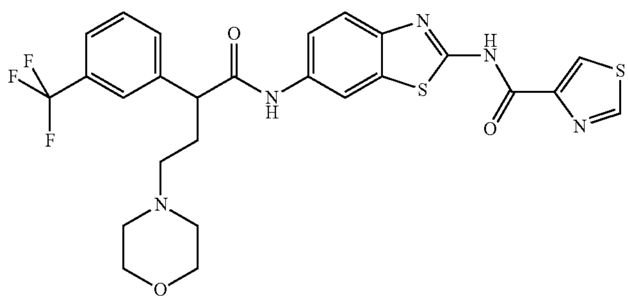 [SMILES: O=C(Nc1nc2ccc(NC(=O)C(CCN3CCOCC3)c3cccc(C(F)(F)F)c3)cc2s1)c1cscn1] | 1.08 | 576.24 | B7 |
| 1171 | 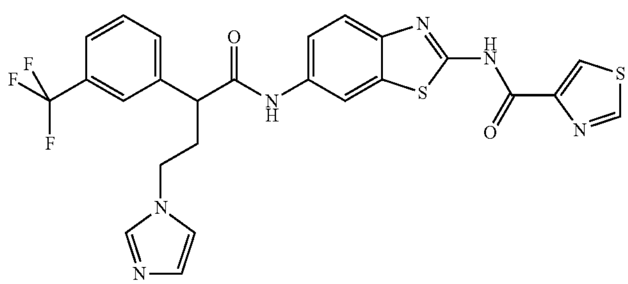 [SMILES: O=C(Nc1nc2ccc(NC(=O)C(CCn3ccnc3)c3cccc(C(F)(F)F)c3)cc2s1)c1cscn1] | 1.09 | 557.21 | B7 |
| 1172 | 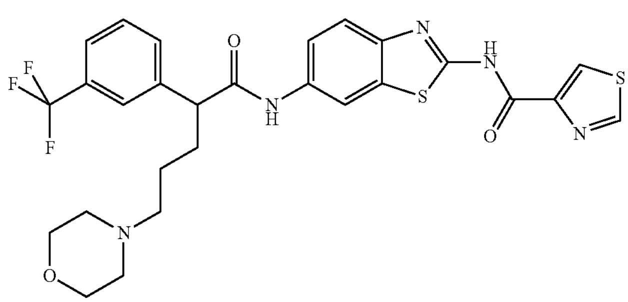 [SMILES: O=C(Nc1nc2ccc(NC(=O)C(CCCN3CCOCC3)c3cccc(C(F)(F)F)c3)cc2s1)c1cscn1] | 1.09 | 590.25 | B7 |

TABLE 1-continued

| Cmpd # | Structure | tR (min) | [M + H]+ | EXAMPLE FOR SYNTHESIS |
|---|---|---|---|---|
| 1173 | 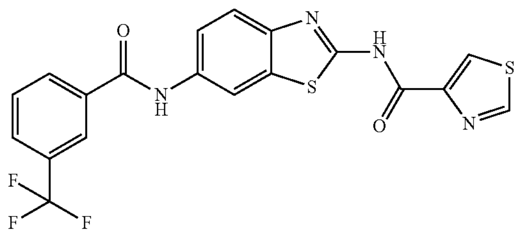 [SMILES: O=C(Nc1ccc2nc(NC(=O)c3cscn3)sc2c1)c1cccc(C(F)(F)F)c1] | 1.43 | 449 | B7 |
| 1174 | 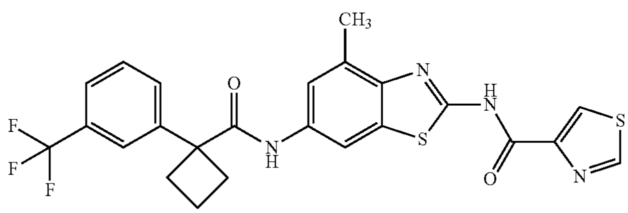 [SMILES: Cc1cc(NC(=O)C2(c3cccc(C(F)(F)F)c3)CCC2)cc2sc(NC(=O)c3cscn3)nc12] | 1.72 | 517.2 | B7 |
| 1175 | 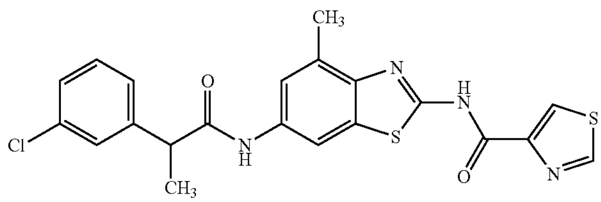 [SMILES: Cc1cc(NC(=O)C(C)c2cccc(Cl)c2)cc2sc(NC(=O)c3cscn3)nc12] | 1.56 | 457.2 | B7 |
| 1176 | 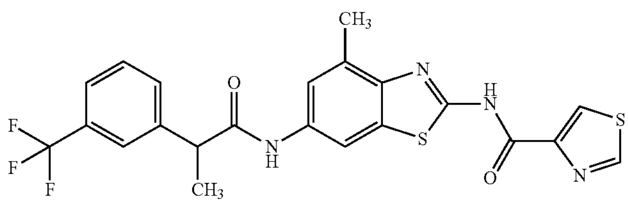 [SMILES: Cc1cc(NC(=O)C(C)c2cccc(C(F)(F)F)c2)cc2sc(NC(=O)c3cscn3)nc12] | 1.6 | 491.2 | B7 |
| 1177 | 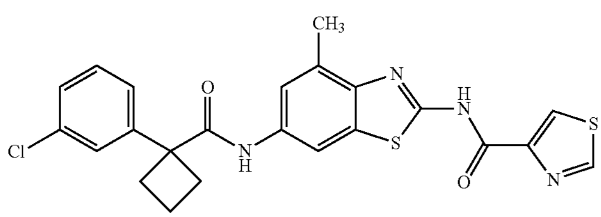 [SMILES: Cc1cc(NC(=O)C2(c3cccc(Cl)c3)CCC2)cc2sc(NC(=O)c3cscn3)nc12] | 1.7 | 483.2 | B7 |
| 1178 | 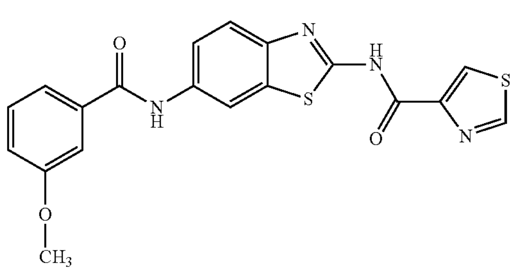 [SMILES: COc1cccc(C(=O)Nc2ccc3nc(NC(=O)c4cscn4)sc3c2)c1] | 1.23 | 411.1 | B7 |

* Pure enatiomer, absoluter configuration unknown.

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of Formula (I) or racemate, enantiomer, diastereomer or tautomer thereof:

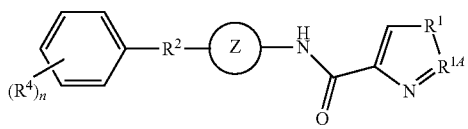

wherein
- $R^1$ is S;
- $R^{1A}$ is CH;
- Ring Z is benzothiazole optionally mono-, di- or tri-substituted with $Z^1$;
  - $Z^1$ is each independently selected from the group consisting of $(C_{1-6})$alkyl, —$(C_{1-6})$alkyl-$(C_{3-7})$cycloalkyl and —O—$(C_{1-6})$alkyl;
- $R^2$ is

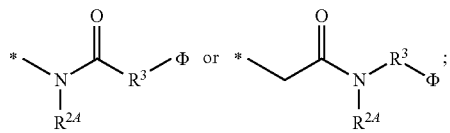

(wherein the site of attachment to the Z ring is indicated with * and the site of attachment to the phenyl ring is indicated with Φ);
- $R^{2A}$ is H or $(C_{1-6})$alkyl;
- $R^3$ is absent, $(C_{3-7})$cycloalkyl or $(C_{1-6})$alkyl optionally mono-, di- or tri-substituted with $R^{3A}$;
  - $R^{3A}$ is each independently selected from the group consisting of halo, OH, —O—$(C_{1-6})$alkyl, —C(=O)OH, —C(=O)NH$_2$, N(H)—C(=O)—O—$(C_{1-6})$alkyl, —$(C_{3-7})$cycloalkyl-C(=O)OH, —O-aryl and —O—$(C_{1-6})$alkyl-aryl;
- $R^4$ is halo, $(C_{1-6})$haloalkyl, —CN, OH, —O—$(C_{1-6})$alkyl or $(C_{1-6})$alkyl,
  - wherein each said alkyl is optionally mono- or di-substituted with OH, C(=O)OH or aryl;
- n is 0, 1, 2 or 3;

or a salt thereof.

2. The compound according to claim 1, having the formula:

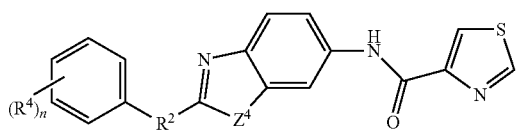

wherein $Z^4$ is S;
or a pharmaceutically acceptable salt thereof.

3. The compound according to claim 1, having the formula:

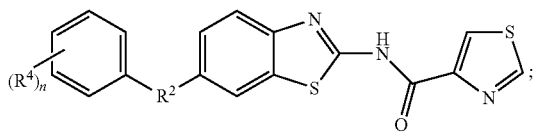

or a pharmaceutically acceptable salt thereof.

4. The compound according to claim 1, wherein $R^2$ is

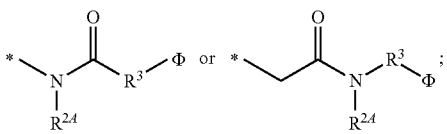

wherein the site of attachment to the Z ring is indicated with * and the site of attachment to the phenyl ring is indicated with Φ;
- $R^{2A}$ is H or $(C_{1-6})$alkyl;
- $R^3$ is absent or $(C_{1-6})$alkyl optionally mono-, di- or tri-substituted with $R^{3A}$;
  - $R^{3A}$ is each independently selected from the group consisting of OH, —O—$(C_{1-6})$alkyl, —O-aryl and —O—$(C_{1-6})$alkyl-aryl;

or a pharmaceutically acceptable salt thereof.

5. The compound according to claim 4, wherein $R^2$ is

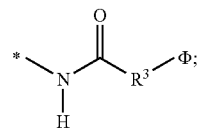

wherein the site of attachment to the Z ring is indicated with * and the site of attachment to the phenyl ring is indicated with Φ;
- $R^3$ is absent or $(C_{1-6})$alkyl optionally mono-, di- or tri-substituted with $R^{3A}$;
  - $R^{3A}$ is each independently selected from the group consisting of OH, —O—$(C_{1-6})$alkyl, —O-aryl and —O—$(C_{1-6})$alkyl-aryl;

or a pharmaceutically acceptable salt thereof.

6. The compound according to claim 1, wherein $R^4$ is halo, $(C_{1-6})$haloalkyl, —CN or $(C_{1-6})$alkyl;

or a pharmaceutically acceptable salt thereof.

7. The compound according to claim 6, wherein $R^4$ is halo or $(C_{1-6})$haloalkyl;
or a pharmaceutically acceptable salt thereof.

8. The compound according to claim 1, wherein n is 0, 1 or 2;
or a pharmaceutically acceptable salt thereof.

9. The compound according to claim 8, wherein n is 1 or 2;
or a pharmaceutically acceptable salt thereof.

10. A method for the treatment of CMV disease and/or infection comprising administering a therapeutically effective amount of a compound according to claim 1 to a patient in need thereof.

11. A pharmaceutical composition comprising a compound according to claim 1, or a pharmaceutically acceptable salt thereof, and a pharmaceutically acceptable carrier.

* * * * *